United States Patent
Aehle (12)

(10) Patent No.: US 6,713,073 B1
(45) Date of Patent: Mar. 30, 2004

(54) METHOD OF VACCINATION OF NEWLY HATCHED POULTRY

(75) Inventor: Sandra M. Aehle, Pacific, MO (US)

(73) Assignee: Megan Health, Inc., St. Louis, MI (US)

(*) Notice: Subject to any disclaimer, the term of this patent is extended or adjusted under 35 U.S.C. 154(b) by 0 days.

(21) Appl. No.: 09/122,299

(22) Filed: Jul. 24, 1998

(51) Int. Cl.$^7$ ...................... A61K 39/112; A61K 39/00; A61K 39/02; A61M 11/00; A01N 63/00

(52) U.S. Cl. ............................. 424/258.1; 128/200.14; 424/93.48; 424/184.1; 424/258.1; 424/826; 435/7.35; 435/235.1; 435/252.8; 435/325

(58) Field of Search .......................................................
Lee, Scientists Testing New Poultry Vaccine Against "Bird Flu", What's New: Press Releases, Protein Sciences Corporation, Apr. 6, 1998.128/200.14; 424/93.48, 184.1, 258.1, 826; 435/7.35, 235.1, 252.8, 325

(56) References Cited

U.S. PATENT DOCUMENTS

| | | | |
|---|---|---|---|
| 4,169,886 A | | 10/1979 | Hertman et al. |
| 4,316,464 A | | 2/1982 | Peterson |
| 4,404,186 A | * | 9/1983 | Ron ............................ 424/92 |
| 4,449,968 A | * | 5/1984 | Peterson ....................... 604/24 |
| 4,674,490 A | * | 6/1987 | Frankel et al. ......... 128/200.14 |
| 5,182,109 A | | 1/1993 | Tamura et al. |
| 5,294,441 A | * | 3/1994 | Curtiss, III ................... 424/93 |
| 5,312,353 A | | 5/1994 | Boggess et al. |

FOREIGN PATENT DOCUMENTS

| | | | | |
|---|---|---|---|---|
| WO | WO 88/09669 | * | 12/1988 | .......... A61K/39/02 |

OTHER PUBLICATIONS

Benjamin. 1995. Live Salmonella Typhi Vaccine Strain, UABRF Dept. of Microbiology.*
Coloe. 1992. PR–22: Use of Aro–*Salmonella typhimurium* as a vaccine in poultry. Victorian Dept. of Food and Agriculture.*
Curtiss, III. 1990. Res. Microbiology 141:797–805.*
Curtiss, III. 1991. Colonization Control of Human Bacterial Enteropathogens In Poultry. 169–198.*
Curtiss, III. 1997. Live Attenuated Vaccines to Control Salmonella and *Eschericha coli* In Poultry, Dept. pf Biology, Washington Univ. and Megan Health, Inc. IVVDC First International Veterinary Vaccines and Diagnostics Conference, Jul. 27–31, 1997, Madison.*
Garavax–T tm *Escherichia coli* Vaccine, Schering Plough Animal Health, Product Bulletin, 1995.*
Grieve. 1997. Poultry Times, Sep. 22, 1997. pp. 18–19.*
LaBudde. salmonella vaccine for poultry. FSNET. Jun. 4, 1997.*
Stewart–Brown. Applying poutry vaccines via the aerosol route on the farm: technique and critique.Solvay Aniaml Health, Inc. 2 pages.*

Al–Tarcha et al., Immunization Of Day–Old Chicks Having Maternally Derived Antibodies Against Infectious Bronchitis: Degree Of Protection As Monitored By Ciliary Activity After Intratracheal Challenge, *Acta Veterinaria Hungarica*, 39:83–93 (1991).
Andreasen, Jr. et al., Studies Of Infectous Laryngotracheitis Vaccines: Immunity In Broilers, *Avian Diseases*, 33:516–523 (1989).
Benjamin, Live Salmonella Typhi Vaccine Strain, UABRF Department of Microbiology, (1995).
Clarke et al., Spray Vaccination Of Chickens Using Infectious Laryngotracheitis Virus, *Australian Veterinary Journal*, 56:424–428 (1980).
Coloe, PR–22: Use Of Aro– *Salmonella typhimurium* As A Vaccine In Poultry, Victorian Department Of Food And Agriculture (1992).
Curtiss, III et al., Stabilization Of Recombinant Avirulent Vaccine Strains In Vivo, *Res. Microbiol.*, 141:797–805 (1990).
Curtiss, III et al., Nonrecombinant And recombinant Avirulent Salmonella Live Vaccines For Poultry, *Colonization Control Of Human Bacterial Enteropathogens In Poultry* 169–198 (1991).
Eidson et al., Application Of The Turkey Herpesvirus Vaccine By The Aerogenic Route For The Prevention Of Marek's Disease, *Develop. Biol. Standard*, 33:370–375 (1975).
Folkers et al., Vaccination Against Avian Encephalomyelitis With Special Reference To The Spray Method, *Develop. Biol. Standard*, 33:364–369 (1975).
Giambrone, Vaccination Methods In The Hatchery, *Hatchery—World Poultry Misset*, 13(7):19–23 (1997).
Ibrahim et al., Spray Vaccination With An Improved F Newcastle Disease Vaccine. A Comparison Of Efficacy With the B1 And La Sota Vaccines, *British Veterinary Journal*, 139:213–219 (1983).
Ibrahim et al., An Assessment Of The Australian V4 Strain Of Newcastle Disease Virus As A Vaccine By Spray, Aerosol And Drinking Water Administration, *Australian Veterinary Journal*, 57:277–279 (1981).
Frazeur, Virogen Hatches New Poultry Vaccine, *AG Innovation News*, 6(4), 3 pages (1997).
Grieve, Administration Of Live Vaccines To Poultry By Spray Is Widely Used, *Poultry Times*, Sep. 22, 1997.
Gross, 4 Colibacillosis, Diseases Of Poultry, Iowa State University Press, 138–144 (1991).
Kramer, Salmonella Vaccine For Poultry, New Vaccine Could Be Solution To Salmonella–Tainted Eggs, Iowa State University Press Release, Jun. 4, 1997.

(List continued on next page.)

Primary Examiner—James C. Housel
Assistant Examiner—Ja-Na Hines
(74) Attorney, Agent, or Firm—Yankwich & Associates; Leon R. Yankwich; Michael R. Wesolowski

(57) ABSTRACT

A method of vaccinating poultry by spraying the poultry with an effective amount of a live avirulent derivative of an enteropathogenic enterobacteria is disclosed.

24 Claims, 7 Drawing Sheets

OTHER PUBLICATIONS

Lee, Scientists Testing New Poultry Vaccine Against "Bird Flu", What's New: Press Releases, Protein Sciences Corporation, Apr. 6, 1998.

Ley et al., Transmissibility Of Live Mycoplasma Gallisepticum Vaccine Strains ts–11 and Jun. 1985 From Vaccinated Layer Pullets To Sentinel Poultry, *Avian Diseases*, 41:187–194 (1997).

Promsopone et al., Evaluation Of An Avian–Specific Probiotic And *Salmonella typhimurium*—Specific Antibodies On The Colonization Of *Salmonella typhimurium* In Broilers, *Journal Of Food Protection*, 61(2):176–180 (1998).

Stewart–Brown, Applying Poultry Vaccines Via The Aerosol Route On The Farm: Technique And Critique, Solvay Animal Health, Inc., 2 pages.

Subramaniam et al., Study Of Immune Status Of Commercial Chicks Against Newcastle Disease Using Live–In–Oil Vaccines With Spray At Day Old, *Indian J. Amin. Hlth.*, 36(1):31–36 (1997).

Toro et al., Infectious Bronchitis: Effect Of Viral Doses And Routes On Specific Lacrimal And Serum Antibody Responses In Chickens, *Avian Diseases*, 41:379–387 (1997).

Toth et al., Reaction Of The Avian Respiratory System To Intratracheally Administered Avirulent *Salmonella typhimurium, Avian Diseases*, 36:24–29 (1992).

Voeten et al., Comparison Of The Effect Of Live Newcastle Disease Vaccine Clone 30 In Broilers Administered At Day 1 Or At Day 7 And The Effect Of H120 Vaccination At 17 Days Of Age: A Field Experiment, *The Veterinary Quarterly*, 38–48.

Wallner–Pendleton et al., Respiratory Infections In Domestic Poultry Flocks, *NebGuide*, G91–1039A (1991).

Yoder, Jr. Diseases Of Poultry Mycoplasm Gallisepticum, *Mycoplasmosis*, 8:208–212.

Paratyphoid Vaccine, *Salmonella Typhimurium* Vaccination Injection For Pigeons, *Vetafarm—Veterinary Articles*, 1 page, Jun. 23, 1998.

Chick Stim, Ostrich Chick Gut Immunostimulant, *Chick Stim*, 1 page, Jul. 1, 1998.

Garavax®–T, *Escherichia coli* Vaccine (Avirulent Live Culture, Avian Isolate), Schering–Plough Animal Health, *Product Bulletin*, (1995).

Spra–Vac, Rhône, Mérieux, Equipment Manual.

Jackwood, Current And Future Recombinant Viral Vaccines For Poultry, Poultry Diagnostic And Research Center, Department Of Avian Medicine, College Of Veterinary Medicine, IVVDC First International Veterinary Vaccines And Diagnostics Conference, Jul. 27–31, 1997, Madison, Wisconsin.

Curtiss, III et al., Live Attenuated Vaccines To Control Salmonella And *Escherichia coli* In Poultry, Department of Biology, Washington University & Megan Health, Inc., IVVDC First International Veterinary Vaccines And Diagnostics Conference, Jul. 27–31, 1997, Madison, Wisconsin.

* cited by examiner

METHOD OF VACCINATION OF NEWLY HATCHED POULTRY

BACKGROUND OF THE INVENTION

1. Field of the Invention

The present invention relates to poultry vaccines and, more particularly, to a novel method of vaccinating poultry involving spraying with a live avirulent derivative of a enteropathogenic bacteria.

2. Description of Related Art

Contamination of poultry meat and eggs by enterobacterial human pathogens, such as Salmonella spp. is a well known cause of illness in humans when such contaminated products are consumed. The contamination occurs predominantly during processing of carcasses after slaughter by contact with intestinal contents that contain high levels of such enterobacteria. The enterobacteria colonize the intestinal tract, but do not normally cause disease in the poultry. In order to reduce the contamination of food with enteropathogens it would thus be desirable to diminish the amount of human enteropathogenic bacteria present in the intestinal tracts of market-age broilers. Efforts to reduce this contamination have focused on improved age broilers. Efforts to reduce this contamination have focused on improved sanitation during production and processing (Bailey, J. S., *Poult. Sci.*, 72:1169–1173, 1993), but such techniques are time-consuming and expensive and are not totally effective in avoiding sporadic contamination. (See, e.g., *Food Borne Disease Outlook Annual Summary*, 1982; and *Salmonella Surveillance Annual Survey* 1992; both available from Center for Disease Control, U.S. Department of Health and Human Services, Atlanta, Ga.). Methods that depend upon sanitation during processing must be repeated frequently since processing equipment and personnel can be re-contaminated by each contaminated fowl that is processed. Methods that depend upon sanitation during production require constant vigilance due the high potential for contamination in the production environment. Therefore, a simple and inexpensive method to control enteropathogenic microbes in poultry during growth would be a key improvement in reducing carcass contamination during processing.

Promosopone et al., *J. Food Protect.*, 61(2): 176–180, 1998, have reported that *S. typhimurium* colonization of the intestinal tracts of poultry can be reduced by administration of an avian-specific probiotic combined with *S. typhimurium* specific antibodies. *Lactobacillus acidophilus*, *Streptococcus faecium* and *S. typhimurium*-specific antibodies were administered by spraying the chicks at one day of age followed by oral administration via the drinking water from day 1 to day 3. The chicks were challenged by oral administration of *S. typhimurium* on day 1 and significantly reduced amounts of *S. typhimurium* were recovered from the cecum and colon following probiotic-treatment at 31, 38 and 43 days. Although administration of probiotic and antibodies as early as 1 day of age may have been important in reducing colonization of the intestine by *S. typhimurium*, it is not clear from this report whether the initial spray administration of probiotic and antibodies or the more commonly used oral administration in the drinking water on days 1–3 was responsible for decreasing *S. typhimurium* colonization.

Vaccines for use in preventing diseases in poultry have been reported and some of these vaccines are specific for Salmonella (See, e.g. U.S. Pat. Nos. 5,294,441, 5,389,368, 5,468,485 and 5,387,744). The methods for administration of vaccines in poultry vary, however, depending upon the target site of action of the active agent. In fact, it is commonly believed that the vaccination route should be tailored according to the preferential site of the microorganism for localization and replication. Thus, for Newcastle disease and infectious bronchitis viruses which multiply in the respiratory route, the vaccination methods of choice would be by eye drop into the eye, nasal passage and respiratory system of the chick or by the spray route. (Giambrone, *World Poultry-Misset* 13:19–23, 1997). Since many of the more important diseases of poultry occur in the respiratory tract, studies reporting on administration of spray vaccination for these diseases have used spray administration because an aerosol or spray is easily inhaled by the bird and thereby contacts the mucosal surfaces of the upper respiratory tract. Administration of vaccines for non-respiratory diseases, such as diseases of the tissues, circulatory system or gut, is usually by subcutaneous injection, or by oral administration, either by inoculation or by application in drinking water.

References disclosing the use of the spray administration of vaccines have almost exclusively been directed to immunizing against viral agents that invade through the respiratory tract such as, for example, to prevent Newcastle disease, avian encephalomyelitis, Marek's disease, laryngotracheitis, infectious bronchitis and the like.

Bacterial vaccines, in particular live attenuated mutants derived from highly virulent bacterial parent strains, have also been used in poultry (Roland, K. et al., Efficacy of *Salmonella typhimurium* vaccine strains expressing *Escherichia coli* 078 lipopolysaccharide to protect against *E. coli* challenge in chickens, Abstract of a presentation at Conf. Of Res. Workers in Animal Diseases, Chicago, Ill., Nov. 10, 1997). Derivation of the attenuated mutant strain from a highly virulent parent increases the likelihood that the attenuated mutant will not only colonize the intestinal tract but also colonize the gut associated lymphoid tissue (GALT) and, elicit protective immunity. (See, e.g., Curtiss III et al., in *Colonization Control of Human Bacterial Enteropathogens in Poultry*, Blankenship et al., eds, Academic Press, Inc., New York, 1991 169–198). In contrast, bacteria that colonize the intestine but do not invade and colonize the GALT may not elicit an immune reaction. For example, studies in mice have revealed that lipopolysaccharide (LPS) O-antigen repeats on the surface of *S. typhimurium* are important not only to withstand nonspecific host defense mechanisms (*Microbial Toxins*, Vol. V, Roantree et al., eds., Academic Press, New York, 1971), but also for effective invasion through the mucin and glycocalyx covering the intestinal tract. As a consequence, rough mutants lacking LPS O antigens, when given orally, are unable to invade and colonize the GALT (See, e.g. Curtiss et al., 1991, supra).

Some references have reported on the administration of bacterial vaccines to poultry by oral or subcutaneous injection. For example, one commercial vaccine to prevent paratyphoid in pigeons comprises killed *S. typhimurium* administered by subcutaneous injection (Vetafarm Paratyphoid Vaccine, Vetafarm Pty. Ltd., Wagga Wagga, Australia). In addition, Curtiss et al, 1991, supra, report the use of an avirulent derivative of a pathogenic Salmonella as an orally administered vaccine in chicks.

Spray vaccination has also been reported for bacterial vaccines that cause respiratory diseases. Hertman et al. report on oral and aerosol administration of a *Pasteurella multocida* vaccine to chickens and turkeys to prevent fowl cholera, which is a respiratory tract disease (U.S. Pat. No. 4,169,886). Ley et al. report on eye-drop and aerosol administration of a vaccine containing live *Mycoplasma*

*gallisepticum*, which produces a respiratory tract disease (Ley et al., *Avian Diseases* 41:187–194, 1997). A commercially available vaccine recommends administration of a vaccine containing an avirulent strain of *E. coli* serotype O78 to immunize against the respiratory disease caused by the wild-type parent (see Product Bulletin for GARAVAX®-T, Schering-Plough Animal Health Corp., Omaha, Nebr.). The use of an aerosol administration for all of these vaccines would have been selected because the underlying disease for which the poultry were being vaccinated involved infection of the respiratory tract.

Another reference reported that a vaccine containing a strain of the nonpathogenic *E. coli* K-12 lacking O-antigen could be administered as an aerosol (U.S. Pat. No. 4,404,186). Nevertheless, the K-12 strain is a laboratory-adapted strain and is not an enteropathogen and because this microbe has no ability to invade and colonize the gut associated lymphoid tissue, it is likely that any immunity elicited by this vaccine would have been due to immunization through the respiratory route.

Localized spraying of bacterial vaccines such as by nasal spraying or ocular spraying had been suggested in some references (for example, see U.S. Pat. No. 5,294,441). Nevertheless, none of this earlier work suggested the use of whole body spray administration of enteropathogenic bacterial vaccines.

Therefore, while spray-administered vaccines have been reported to be useful in controlling respiratory diseases in poultry, whole-body spray administration has not been suggested for vaccines in poultry for the control of human pathogens that are often present in and transmitted by poultry, but which are not the causative agents for respiratory disease in poultry.

Accordingly, it would be desirable to provide a method of reducing the contamination of poultry by enteropathogenic microbes, especially Salmonella spp., that would be easy and inexpensive to administer under normal commercial poultry production conditions; which could be administered to newly hatched chicks without individual handling; and which would reduce or prevent infection of visceral and lymphatic tissues and the intestinal tract of poultry by enteropathogenic microbes.

SUMMARY OF THE INVENTION

In accordance with the present invention, it has been discovered that vaccines can be administered to domestic birds by whole-body spraying of the birds with the vaccine. The vaccines are administered by this whole-body spray route in an amount that is effective in eliciting an immune response, i.e. antibody and/or cellular immunity. While virtually any vaccine can be delivered by this method, whole-body spray administration is surprisingly effective for vaccines comprising a live avirulent derivative of an enteropathogenic bacteria. Such enteropathogenic bacteria are preferably Salmonella species. This spray administration of enteropathogenic bacteria avoids some of the disadvantages of other routes of administrations in that it does not require individual handling of chicks, it can be administered on day-of-hatch, and is easy to use under conditions normally found in commercial poultry production.

The effective doses, which elicit an immune response, are unexpectedly low and roughly comparable to doses that are effective by the oral route of administration, such as administration in the drinking water. Typically, doses for administration of the live vaccines of the present invention are from about $10^5$ to about $10^8$ colony forming units.

The spray route of administration of the vaccines is applicable to vaccination of birds, such as chickens, at any age at which they are susceptible to the beneficial effects of the vaccine, but is especially applicable to birds that are of an age of 3 weeks or less, and, preferably, to birds of less than 1 day of age.

In some embodiments, the spray-administration can be followed by administration of the vaccine in at least one booster dose. Preferably such a booster dose can be administered orally by drinking water or by spray at about 14 days after administration by spray.

Preferably, the spray is a coarse spray of droplets having diameters in the range of from about 50 microns to about 150 microns.

In other embodiments the present invention is directed to a method for reducing microbial contamination of poultry. The method comprises immunizing the poultry against a microbial contaminant by whole-body spray administration of an immunogenic composition. The microbial contaminant may or may not be pathogenic to the poultry itself, however, when present in the poultry, such microbial contaminates can produce disease symptoms in humans consuming the meat or other food products produced from the poultry. The microbial contaminant can be any such contaminant, particularly, microbes that colonize the gastrointestinal tract of the poultry.

The immunogenic composition is administered in an amount that is effective in eliciting an immune response, i.e. antibody and/or cellular immunity against the microbial contaminant. Preferably, the immunogenic composition comprises a live avirulent derivative of an enteropathogenic bacteria. Such enteropathogenic bacteria are preferably Salmonella species.

The immunogenic composition is administered in doses, which are effective in eliciting an immune response. Such doses are roughly comparable to doses that are effective by the oral route of administration. Typically, doses for administration of the live vaccines of the present invention are from about $10^5$ to about $10^8$ colony forming units.

The spray route of administration of the immunogenic composition of the present invention is applicable to vaccination of birds of any age at which they are susceptible to the beneficial effects of the vaccine, but is particularly applicable to birds, such as chickens, at an age of 3 weeks or less, and, preferably, to birds of less than 1 day of age.

In some embodiments, the spray-administration can be followed by administration of the immunogenic composition in at least one booster dose by oral administration in the drinking water, preferably at about 14 days after administration by spray.

The spray is, preferably, a coarse spray of droplets having diameters in the range of from about 50 microns to about 150 microns.

Among the several advantages found to be achieved by the present invention, therefore, may be noted the provision of a new method for vaccinating a domestic bird using an enteropathogenic bacteria; the provision of a method for reducing the amount of colonization of the intestinal tract, lymphatic tissues and visceral tissues by enteropathogenic microbes, the provision of a method for reducing the microbial contamination of poultry destined for human consumption; the provision of a method that is easy and inexpensive to administer under normal commercial poultry production conditions; and the provision of a method that that allows administration to young, especially day-of-hatch chicks without individual handling.

Figure 1A:
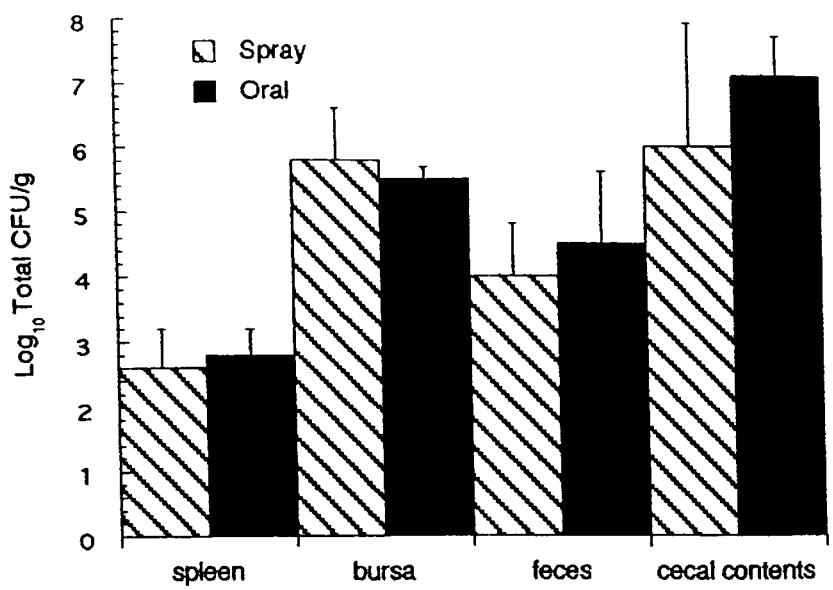
FIG. 1 shows the recovery of S. typhimurium χ3985 vaccine strain from the spleen and bursal tissues, feces and cecal contents of white leghorn chicks 7 days after receiving (a) $10^5$ CFU, (b) $10^7$ CFU, or (c) $10^9$ CFU of χ3985 by coarse spray or by direct oral methods of delivery on day of hatch.
Figure 1B:
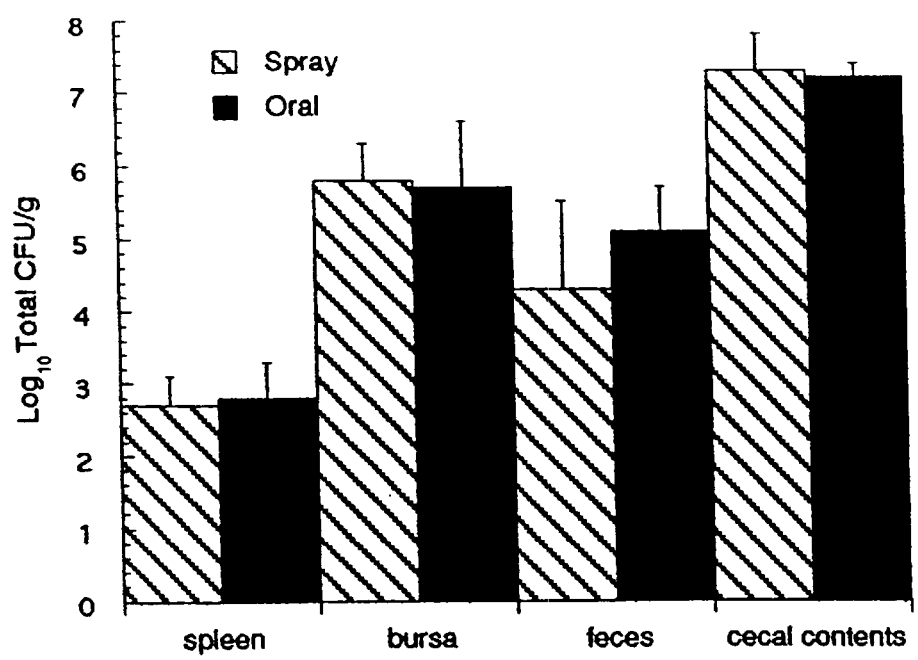
Figure 1C:
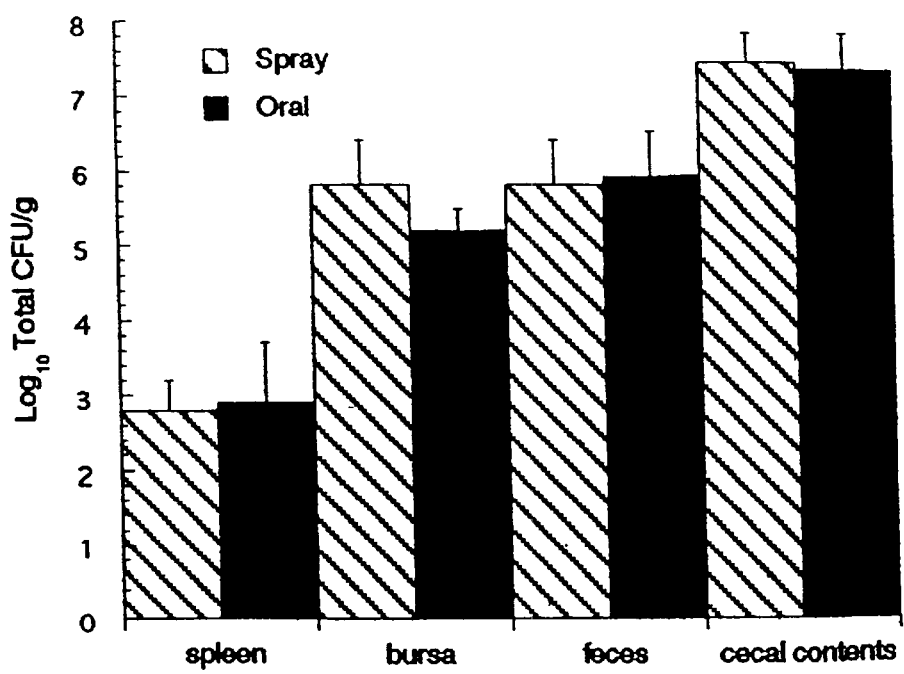
Figure 2A:
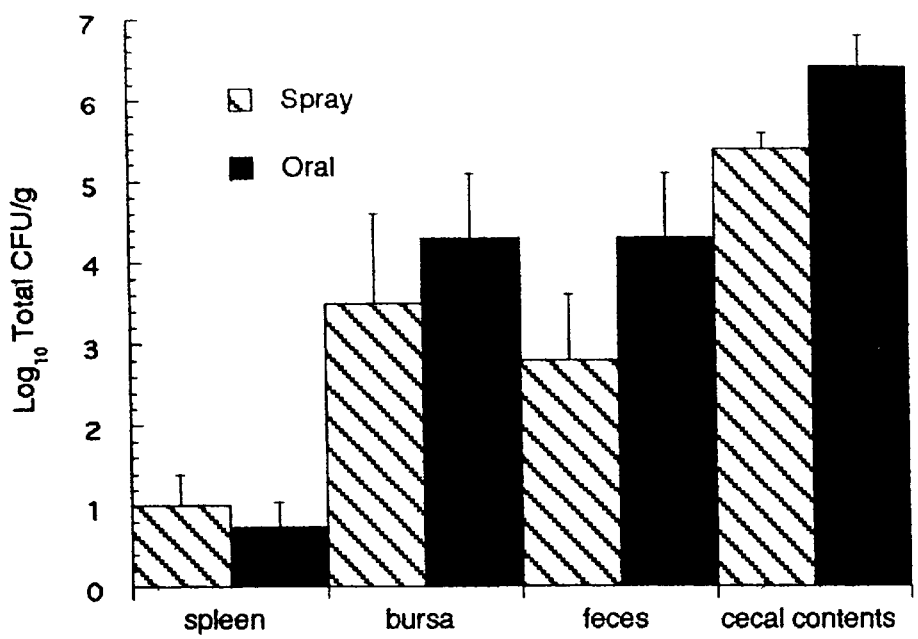
FIG. 2 shows the recovery of S. typhimurium χ3985 vaccine strain from the spleen and bursal tissues, feces and cecal contents of white leghorn chicks 20 days after receiving (a) $10^5$ CFU, (b) $10^7$ CFU, or (c) $10^9$ CFU of χ3985 by coarse spray or by direct oral methods of delivery at days 1 and 14.
Figure 2B:
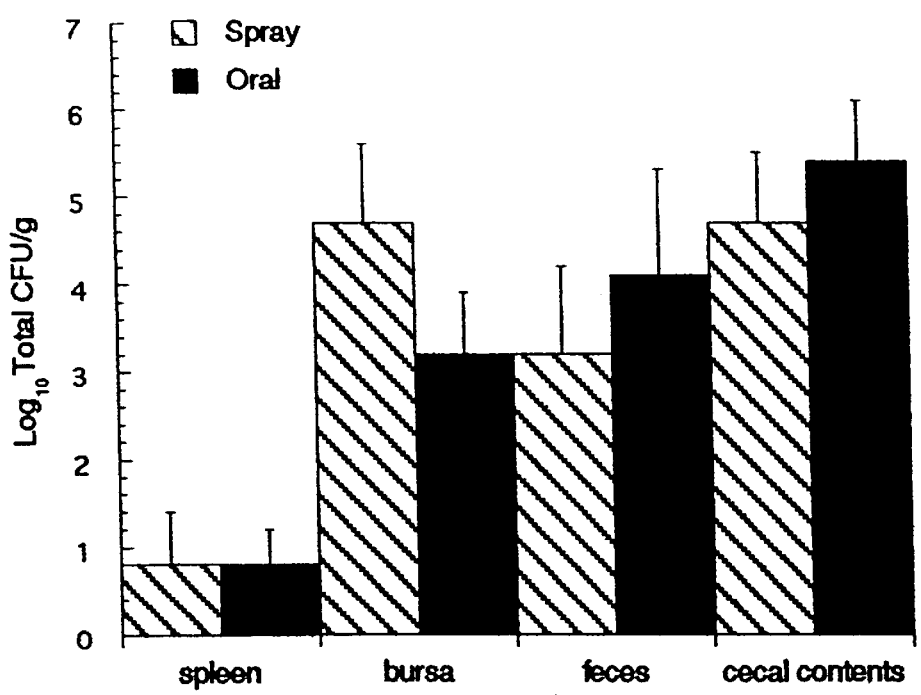
Figure 2C:
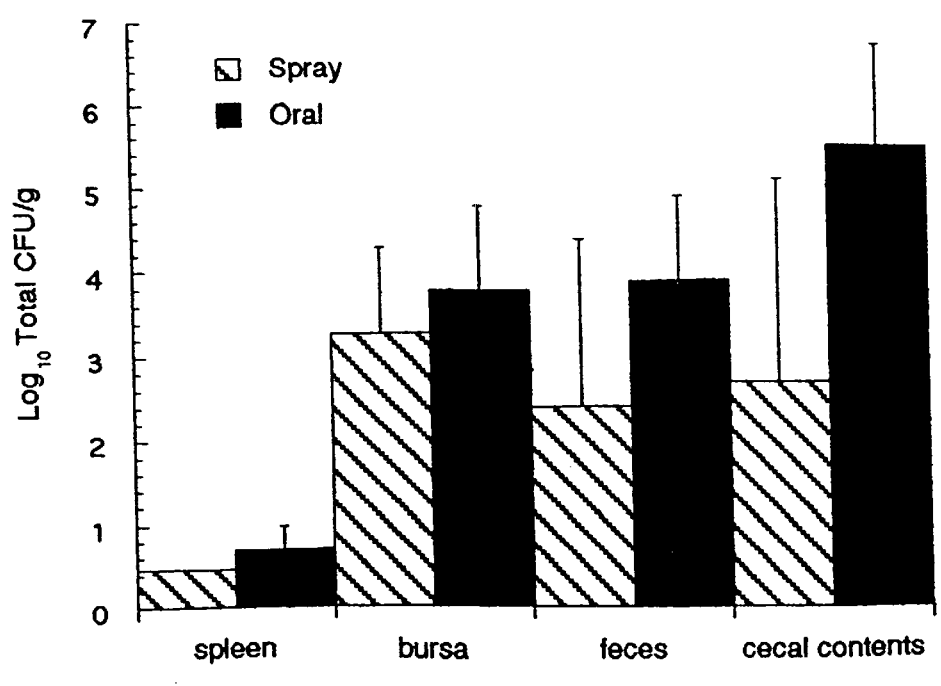
Figure 3A:
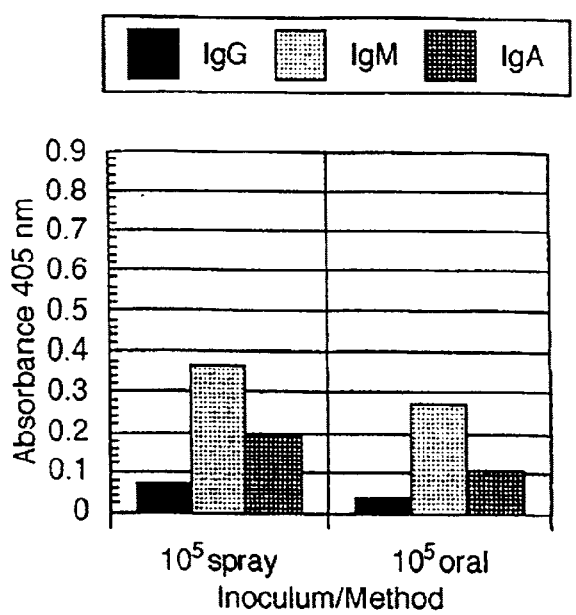
FIG. 3 shows the serum IgM, IgA and IgG responses at 20 days of age as detected by using purified S. typhimurium LPS in white leghorn chickens immunized and boosted with (a) $10^5$ CFU, (b) $10^7$ CFU, or (c) $10^9$ CFU of S. typhimurium χ3985 by coarse spray or by direct oral methods of delivery at days 1 and 14.
Figure 3B:
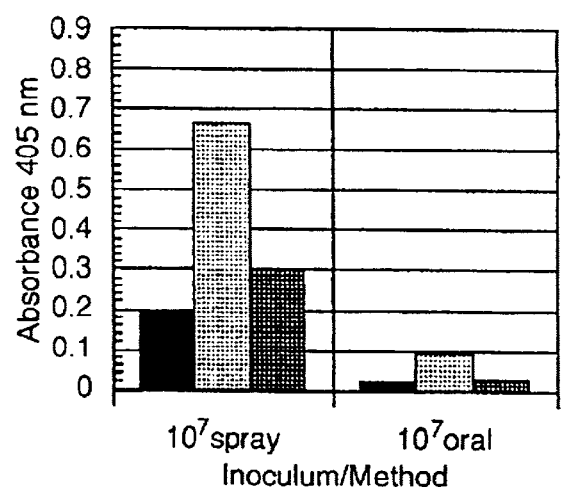
Figure 3C:
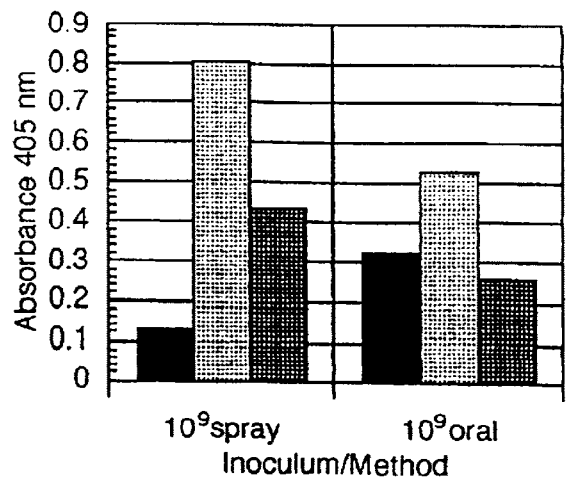

DESCRIPTION OF THE PREFERRED EMBODIMENTS:

The present invention is based upon the discovery that whole-body spray administration can be used to deliver vaccines or immunogenic compositions of live avirulent derivative of an enteropathogenic bacteria to domestic birds and effectively elicit an immune response.

The whole-body spray administration of the present invention allows delivery of the vaccine or immunogenic compositions to the gastrointestinal tract of the poultry. Spray administration or spray vaccination as used herein is intended to mean the delivery of droplets of a liquid comprising a vaccine or immunogenic composition. Whole-body spray administration is intended to mean the delivery of such droplets of vaccine or immunogenic composition to a large portion of the entire body of the poultry. This in contradistinction to a localized spray administration such as is by intranasal spraying in humans in which administration is to only a specific, small, localized target area. The whole-body spray approach for administering enteropathogenic bacteria of the present invention indiscriminately delivers the vaccine microbe to a large portion of the body surface of the poultry constituting that portion of the entire body surface that is accessible to the spray device (see for example, U.S. Pat. Nos. 4,316,464 and 4,449,968 which are incorporated by reference). Such whole-body spray administration of the vaccines or immunogenic compositions of the present invention is particularly applicable for administration to large numbers of poultry at the same time.

Spray administration in the present invention preferably involves delivery of a coarse spray containing the vaccine or immunogenic composition to the poultry. Although not wishing to be bound by a particular theory, it is believed that the administration of a vaccine or immunogenic composition as a coarse spray allows the spray droplets to contact the body surface while minimizing the amount of the vaccine that is inhaled into the lower respiratory system. This is to be distinguished from a spray of very fine droplets or mist, such as is commonly referred to as an aerosol in which droplets have a diameter of less than about 40 microns. Unlike the aerosol sprays, the coarse spray of the present invention is believed to not be deeply inhaled which assists in avoiding the development of respiratory infections seen with some spray vaccination (See for example, U.S. Pat. No. 4,449,968; Clarke et al, *Austr. Vet. J.* 56:424–428, 1980). A coarse spray as used herein is intended to mean a spray that is composed of liquid droplets having a diameter sufficient to substantially prevent the inhalation of the droplets into the lower respiratory system of the bird, but still causing the liquid droplets to contact the body surface of the bird. The consistency of such a coarse spray has been referred to as "misty rain", and it is preferred that the spray have less than about 1% of the droplets in a size range of less than about 12 microns. Preferably, the coarse spray is composed of droplets having a mean diameter of from about 40 to about 400 microns; more preferably from about 40 microns to about 200 microns, even more preferably from about 50 to about 150 microns and most preferably from about 50 to about 100 microns. Alternatively the coarse spray can have about 80% of droplets in a range of from about 90 to about 190 microns.

The type of spray vaccination equipment that is used for the administration of the vaccine is not critical and almost any type of spray vaccination equipment capable of dispensing a coarse spray can be used (see for example, U.S. Pat. Nos. 4,316,464, 4,449,968, 4,674 and 5,312,353).

The spray administration of the present invention delivers a vaccine comprising a live avirulent derivative of an enteropathogenic bacteria. The vaccine microbe is an enterobacteria capable of colonizing the intestinal tract and gut associated lymphoid tissues (GALT) of the poultry. Such microbes serve as the immunogenic component of the vaccine or immunogenic composition and include Enterobacteriaceae family members such as Escherichia, Klebsiella, Proteus, Yersinia, and Erwinia. In particular, Salmonella, Escherichia and Salmonella-Escherichia hybrids are useful in the present invention, including, preferably, *E. coli* and Salmonella such as *S. typhimurium*, *S. typhi*, *S. paratyphi*, *S. enteritidis*, *S. dublin*, *S. gallinarum*, *S. pullorum*, *S. arizona*, and *S. choleraesuis*.

The avirulent derivative of an enteropathogenic bacteria can also serve as a carrier bacterium to deliver selected antigens to the GALT. Such carrier bacteria that contain and express a recombinant gene from a pathogenic organism so that antibodies and/or cellular immunity will be elicited against the antigenic gene product normally produced by the pathogenic organism. It is thus possible to use the avirulent derivative of an enteropathogenic bacteria, administered by spray, to deliver antigens to a wide variety of microbes and to elicit an immune response in the poultry against microbes that need not necessarily be able to colonize the gastrointestinal (GI) tract.

The avirulent microbes can additionally be used as vectors for the synthesis of various proteins in the poultry. Because the avirulent microbes of this invention are able to traverse the GALT after spray administration and entry into the gastrointestinal tract of the poultry, the microbes can be used to make and deliver gene products such as, for example, growth factors or immunoregulatory products or substances that stimulate or suppress various physiological functions. Such microbes contain and express a recombinant gene that encodes the desired protein.

The terms enteropathogenic bacteria are intended to mean microbes that are capable of colonizing the intestinal tract and the gut associated lymphoid system of the poultry. As used herein, pathogen is intended to mean a microbe that is capable of causing disease symptoms or impairing normal physiological functioning. The vaccines of the present invention contain avirulent derivatives of an enteropathogenic strain of bacteria. By derivative or derived strain reference is made to a strain that has been genetically modified from its parent from which it is descended. By pathogenic it is meant that the microbe is capable of causing disease or impairing normal physiological functioning. Reference to avirulence is intended to mean that a particular microbe strain is incapable of inducing a full suite of symptoms of the disease state that is normally associated with its virulent pathogenic counterpart. Thus, avirulence includes a state of diminished virulence or ability to produce disease conditions and the avirulent microorganisms are not necessarily completely absent of any ability to impair normal physiological functioning of the host. In addition, an avirulent microbe is not necessarily incapable of ever functioning as a pathogen, but the particular microbe being used is avirulent with respect to the particular individual being treated. Preferably, the enteropathogenic bacteria from which the avirulent microbe is derived is pathogenic at least to day-of-hatch birds.

In a preferred embodiment of the present invention, the live avirulent derivative of an enteropathogenic bacteria is an *S. typhimurium*, such as χ3985, which has Δcya-12/Δcrp-11 mutations. This construction of this and other strains is described in detail in U.S. Pat. No. 5,294,441.

An immunological response to a composition or vaccine is the development in the host of a cellular and/or antibody-mediated immune response to the composition or vaccine of interest. Usually, such a response consists of the subject producing antibodies, B cells, helper T cells, suppressor T cells, and/or cytotoxic T cells directed specifically to an antigen or antigens included in the composition or vaccine of interest.

By vaccine is meant an agent used to stimulate the immune system of an individual so that protection is provided against an antigen not recognized as a self-antigen by the immune system. Immunization refers to the process of inducing a continuing high level of antibody and/or cellular immune response in which T-lymphocytes can either kill the invading microbe and/or activate other cells (e.g., phagocytes) to do so in an individual, which is directed against a microbe or antigen to which the organism has been previously exposed. The phrase immune system is intended to refer to the anatomical features and mechanisms by which an individual produces antibodies against an antigenic material which invades the cells of the individual or the extracellular fluid of the individual and is also intended to include cellular immune responses. In the case of antibody production, the antibody so produced can belong to any of the immunological classes, such as immunoglobulins, A, D, E, G or M. Of particular interest are vaccines which stimulate production of immunoglobulin A (IgA) since this is the principle immunoglobulin produced by the secretory system of warm-blooded animals, although vaccines of the invention are not limited to those which stimulate IgA production. For example, vaccines of the nature described herein are likely to produce a broad range of other immune responses in addition to IgA formation, for example cellular and humoral immunity. Immune responses to antigens are well studied and widely reported. A survey of immunology is provided in Elgert, Klaus D., *Immunology,* Wiley Liss, Inc., (1996); Stites et al., *Basic & Clinical Immunology; 7th* Ed., Appleton & Lange, (1991) the entirety of which are incorporated herein by reference.

An individual treated with a vaccine of the present invention is intended to mean one of a species of birds, including domestic birds, particularly those of agricultural importance. Domestic birds or poultry as used herein includes any of a variety of domesticated avian species or individuals of that species, such as chickens, turkeys, ducks, geese, pigeons, guineas, ostriches, emus, and the like and, in particular, those domesticated avian species or individuals kept for the production of eggs or meat.

The vaccine can be prepared by growing the vaccine strain in suitable growth media and then used as is or formed into a vaccine composition by combining the growing culture, or the cells therefrom, with a suitable diluent. Suitable diluents are preferably liquids and are more preferably a liquid that does not adversely effect the stability and vitality of the vaccine culture and which has a viscosity similar to water so that it will easily form droplets of a coarse spray. The diluent is preferably free of chlorine, antibiotics, antimicrobials, or any other agent that may be harmful to the live vaccine organisms. Vaccine should be dispersible in the diluent so that no solid lumps or chunks of vaccine remain and the diluent should be at a temperature that is not harmful to the live vaccine microbes. Examples of suitable diluents include water, distilled water, de-ionized water, skim milk, water containing Marek's vaccine stabilizer, buffered saline with gelatin, and similar compositions that are well-known to persons of skill in the art. The vaccine is preferably introduced into the diluent while the diluent is at a temperature of approximately room temperature or cooler more preferably from about 34° C. to about 15° C.

In one embodiment, vaccine is prepared from S. typhimurium UK-1 Δcya Δcrp χ3985. As used herein, this vaccine may be referred to as χ3985, or as Chi3985, or as χ3985, Production Code 19C1.01. The vaccine strain can be freshly prepared as described above, or may be recovered from a culture stored, for example, as a freeze-dried culture, in a frozen form (for example, as −70° C. working seed stock), or otherwise. An inoculum from such culture is then grown to a late log-phase culture in Luria broth in 37° C. By way of example, a −70° C. seed stock can be used to inoculate 50 ml of Luria broth in a 250 ml sterile flask covered loosely with foil. The flask is incubated as a static culture at 37° C. overnight. After about 12–24 hr., 50 ml of the static overnight culture is pipetted into 450 ml of prewarmed Luria broth in a 1 L nonbaffled flask at 37° C. and placed in a New Brunswick incubator shaker at 150 rpm. After the culture reaches $OD_{600} \geq 1.0$, cells are pelleted by centrifugation (4400 rpm, 15 min in a Centra MP4 centrifuge, IEC swinging bucket 3224 rotor) at room temperature. Cells are resuspended in 40 ml of room temperature buffered saline with gelatin (BSG). The titer of the vaccine composition can be determined by serially diluting the cell suspension 10-fold in BSG and spreading 100 µl of $10^{-6}$ and $10^{-7}$ dilutions onto MacConkey agar +1% maltose for plating. The titer of the vaccine strain is then determined by counting colonies that develop upon incubation of the plates. The titer is expressed in terms of colony forming units of the vaccine microbe (CFU) per unit volume of the vaccine composition.

Vaccine for application to poultry is prepared as described above and the culture is diluted to the desired dose density, or titer, in a suitable diluent. The buffer of the diluent, if used, is adjusted to match the pH and ionic strength required to maintain the stability and vitality of the vaccine strain. The vaccine is then ready for loading into the sprayer and for administration to the poultry.

Spray administration can also be performed in a manner to deliver a particular dosage per bird. One technique that can be used to deliver an accurate vaccine dosage is to spray birds in an enclosed space for a calculated period of time at a known volumetric delivery rate. By knowing the number of birds to be vaccinated, the desired dosage of the vaccine per bird, the titer of the vaccine and the delivery rate of the spray equipment, one skilled in the art can easily calculate the spraying time required to deliver the required dosage per bird. Furthermore, some models of commercially available spray equipment allow pre-selection of the volume of liquid to be delivered to a known number of birds.

The vaccine or immunogenic composition of the present invention is administered in an effective dose or an effective amount. As used herein an effective amount is that quantity of vaccine or immunogenic composition which is sufficient to elicit an immune response against a target microbe or antigen for which the poultry is being vaccinated. Such immune response will involve the production of antibodies and/or cellular immunity. In one significant aspect of the present invention, the vaccine or immunogenic composition can be administered at a dose roughly equal to the dose effective upon oral administration, for example by administration in the drinking water.

Preferably the spray administration is given to birds when they are less than one day old, i.e. on the day of hatch. It is often also desirable to administer one or more booster applications of the vaccine some time after the initial spray administration. Such booster applications can be administered at any time during the bird's life at which the bird is susceptible to the beneficial effects of the vaccine. Preferably, such booster applications are applied between 5 and 21 days of age, more preferably between 6 and 15 days of age and still more preferably between 7 and 14 days of age and most preferably at 7 days of age or 14 days of age or at both 7 and 14 days of age.

The booster doses are typically administered orally in the drinking water although the booster dose can be administered by any route including by spray administration. Administration of the vaccine in the drinking water can be performed by any of a number of methods known in the art. By way of example only, administration in the drinking water can be performed using the following method. First all disinfectants, sanitizers and antimicrobials are removed from the drinking water being given to the birds 24 hours prior to vaccine administration. Such water free of disinfectants, sanitizers and antimicrobials is again given 24 hours after vaccination. The vaccine can then be mixed in the clean water that contains no sanitizing agents or antimicrobials. Fifty liters of vaccine-containing water can be used for 500 birds such as chickens and ample space should be provided for all birds to drink easily. Water containing vaccine should be consumed in 2 hours or less. To assure that all birds drink, water should be withheld for one to two hours prior to administration in the drinking water.

Because the dosage amount for spray administration of the vaccine or immunogenic composition is approximately the same as the oral dose in the drinking water, both dosage amounts are, preferably, about the same. Thus, for example, if $10^7$ colony forming units are administered per bird by spray administration, then, preferably, about $10^7$ colony forming units are administered per bird in the drinking water. Preferably, the initial spray administration dose and any subsequent booster dose administered in the drinking water will differ by less than 100 fold, more preferably by less than 10 fold, even more preferable by less than three fold and still more preferably by less than 10%.

It is preferred that the poultry to be vaccinated be of an age at which it is susceptible to the beneficial immunogenic effects of the vaccine. While this may vary with species, it has been found that, such beneficial effects are obtained in poultry that is of an age of from hatching to about 104 weeks of age. It is preferred that poultry be day-of-hatch to 52 weeks of age, more preferably from day-of-hatch to 3 weeks of age, even more preferably day-of-hatch to 2 weeks of age, still more preferably day-of-hatch to 1 week of age and most preferably that it be day-of-hatch. As used herein, the phrase "day-of-hatch" may be used interchangeably with the term "less than one day of age".

One advantage of the present method is that it is amenable to application under conditions that normally occur in commercial poultry raising operations. Typically, large commercial chicken or turkey raising operations are characterized by large poultry houses having more or less automated feed and watering systems and housing over 1,000 birds per house; often over 5,000 birds per house and even over 20,000 birds per house.

The present method can be used at the hatchery or at the poultry farm on newly hatched chicks by spraying the chicks in the chick boxes, or other trays or boxes, prior to their release into the brooder house or poultry house. Alternatively, either young or older poultry can be sprayed after release into the house. (See, e.g., Grieve, *Poultry Times*, p.18, Sep. 22,1997; and Giambrone, 1997, supra.)

Because of the ease of application of the present method, the cost of poultry vaccination can be very low. The high cost of individual chick handling is avoided by the ability to vaccinate dozens of chicks at one time and in a matter of seconds. Moreover, the accurate administration of the dosage of the vaccine to each chick minimizes overdosing and inefficient application of the vaccine.

The following examples describe preferred embodiments of the invention. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

EXAMPLE 1

This example illustrates that spray vaccination of young chicks with a live *S. typhimurium* vaccine was as effective as direct oral administration of the vaccine in inducing serum immunity and in producing colonization of the intestinal tract and visceral tissues by the vaccine microbe and in inducing serum immunity.

To determine the efficiency of colonization and induction of immunity by a live avirulent Δcya Δcrp mutant *S. typhimurium* vaccine the present study investigated the use of a coarse spray as a means to deliver the primary and booster vaccinations to day-old chicks. Duplicate groups of birds were given the vaccine by the oral route. In addition, two smaller groups of birds were given the wild-type *S. typhimurium*, UK-1 MGN-054s, by the spray and oral inoculation methods and $LD_{50}$'s were determined. Colonization of the spleen, bursa, intestinal tract and cecum by the vaccine strain at 7 and 20 days of age was determined for the groups of birds receiving the vaccine strain by the coarse spray route and the direct oral method of delivery. Serum antibody responses were measured by ELISA for sera recovered from 20-day-old vaccinates.

Objective:

The goals of the study were: 1) to determine if young chicks vaccinated by using a coarse spray method of vaccination are as efficiently colonized by the vaccine strain compared to chicks vaccinated by the direct oral route of vaccination, and 2) to evaluate serum immunity elicited by escalating doses of the vaccine given by either coarse spray of oral administration. Since a lethal endpoint can be determined in day-old chicks (but not in 3-day-old or older chicks), the wild-type *S. typhimurium* parent strain was included to determine if both methods of delivery could efficiently and comparably cause disease.

Materials and Methods:

*S. typhimurium* UK-1 Δcya-12 Δcrp-11 χ3985 is an attenuated vaccine strain (see Curtiss III, et al., in *Colonization Control of Human Bacterial Enteropathogens in Poultry*, Blankenship et al., eds. Academic Press, New York, 1991, pp. 169–198). This strain was grown as a fresh late log-phase Luria broth culture and subsequently diluted in buffered saline with gelatin to the desired dose density. The vaccine was prepared to deliver escalating doses of about $10^5$, $10^7$ and $10^9$ CFU (colony forming units) to groups of 4 one-day-old white leghorn chicks. The chicks were treated with either coarse spray (droplets of approximately 140 micron diameter) using a spray vaccination device (Preval Power Unit, Precision Valve Corporation, Yonkers, N.Y., 10703) or by direct oral vaccination administered with an 18 gauge×7.5 mm feeding needle with a 3 mm ball attached at the end. Birds were maintained on Purina Start and Grow without coccidiostats or antibiotics.

Concurrently, escalating doses of the wild-type *S. typhimurium* parent strain MGN-054s were prepared in buffered saline with gelatin from a fresh late log-phase Luria broth culture and administered to groups of 3 day-of-hatch white leghorn chicks by either coarse spray or by direct oral delivery.

All groups of birds that received the vaccine strain on day-of-hatch were administered a booster inoculation on day 14 by the same route and dosage as used per individual group for the primary inoculation. At 7 and 20 days of age, groups of birds were euthanized with $CO_2$ asphyxiation and necropsies performed to aseptically recover samples of the spleen and bursa, fecal matter and cecal contents for enumeration of the vaccine strain.

Serum was separated from blood collected during the 20-day necropsy and diluted 1:200 for ELISA. Briefly, purified LPS from *S. typhimurium* was used as the test antigen. Goat anti-chicken IgA, IgM and IgG affinity-purified polyclonal antibodies EC2-001, EC2-005 and EC2-0011, respectively, (from Immunovision, Springdale, Ark.) were used at a dilution of 1/5000 to detect chicken IgM, IgA or IgG bound to purified LPS antigen on ELISA plates (Dynatech Laboratories Inc., Alexandra, Va.). A rabbit anti-goat IgG (whole molecule) alkaline phosphatase conjugate (Sigma, St. Louis, Mont.) was used at a dilution of 1/3000 with P-nitrophenyl phosphate (Sigma, St. Louis, Mont.) (1 mg/ml) in diethanolamine buffer pH 9.8 as the substrate. The reaction was stopped after 30-min. incubation with 50 μl of 3M sodium hydroxide. Absorbancies were read at 405 nm using an automated microplate reader (Bio-Tek, Winooski, Vt.). The ELISA results were expressed as mean absorbance (405 nm) of four chickens within a treatment group. The cut-off point was taken as 2× the mean of the absorbance of sera from noninfected chickens which served as the baseline for the detection of chicken immunoglobulin isotypes by ELISA.

Results and Conclusion:

No mortality was observed in groups of birds that received doses of the vaccine up to $10^9$ CFU administered by on days 1 and 14. The $LD_{50}$'s observed in the groups of day-old chicks that received escalating doses of the wild-type virulent parent strain by the coarse spray or oral method of delivery were approximately $10^3$ CFU, which were the same as previously determined by oral inoculation in day-old chicks.

FIG. 1(*a, b* and *c*) shows recovery of the vaccine strain from the spleen and bursal tissues and feces and cecal contents of birds 7 days after receiving the vaccine strain on day-of-hatch. FIG. 2(*a, b* and *c*) shows recovery of the vaccine strain from the spleen and bursal tissues and feces and cecal contents of birds 20 days after receiving the vaccine strain on days 1 and 14. The vaccine strain colonized visceral and lymphatic tissues as well as the intestinal tract efficiently in 100% of the birds sampled. In another study comparing these two methods of vaccine delivery, similar results were observed with broiler chicks maintained on Purina Start and Gro supplemented with the recommended levels of bacitracin (BMD-50) and a coccidiostat (Coban-100). For all dose levels compared, the data generally showed no significant differences between the use of coarse spray or direct oral inoculation to deliver the *S. typhimurium* χ3985 vaccine strain to leghorn or broiler birds.

The levels of Salmonella-specific IgM, IgA and IgG detected by ELISA against *S. typhimurium* LPS in chickens administered the vaccine χ3985 are presented in FIG. 3. Doses ranging from $10^5$ to $10^9$ CFU induced significant humoral antibodies using either delivery method tested. The highest dose of $10^9$ CFU induced the greatest antibody response compared to the lower doses. IgM was the predominant immunoglobulin at 20 days of age in all birds tested in all dose groups. It has been reported that IgM is the predominant isotope 3 weeks post-vaccination by the oral routes. (Hassan and Curtiss, *Res. Microbiol.,* 141:839–850, 1990). Increased antibody responses, which are reflected by higher $OD_{405}$ measurements, were observed in the present study in birds that received $10^7$ or $10^9$ CFU by spray compared to birds that received $10^7$ or $10^9$ CFU by direct oral method of delivery.

EXAMPLE 2

This example shows the efficacy of spray vaccination of a live avirulent *S. typhimurium* vaccine in preventing colonization of the GI tract and intestinal organs by wild-type *S. typhimurium.*

Fifty-five one-day-old SPF white leghorn chicks were wing banded for use in this trial. At day-of-age, 30 birds were vaccinated by coarse spray with $1\times10^7$ CFU per dose of *S. typhimurium* vaccine carried in approximately 0.3 ml per bird using a Preval Power Unit spray device, from Precision Valve Corp., Yonkers, N.Y. 10703. The vaccine was χ3985, Product Code 19C1.01 (Maine Biological Laboratories, Inc., Waterville, Me.). Twenty birds received 0.3 ml per bird of distilled water by coarse spray and served as controls. Five additional birds were held as contemporary controls. Vaccinates and controls were housed separately in Horsfal isolation units. At two weeks of age, the vaccinates were boosted in the drinking water with $1\times10^7$ CFU per dose of the same vaccine. At six weeks of age all birds in both treatment groups were individually challenged with an oral dose of $1\times10^6$ CFU in 0.1 ml of wild type *S. typhimurium.*

Cloacal swabs were collected from each bird of both treatment groups prior to challenge and at the time of sacrifice to monitor for Salmonella sp. Swabs were placed in 5 ml of TBGH broth and incubated for 24–36 hours at 42° C. After about 36 hours, the broth was streaked onto brilliant green agar +35 μg/ml novobiocin (BGAN) and incubated at 42° C.

At seven weeks of age all birds were euthanized and tissues were recovered and cultured for the wild type *S. typhimurium* as follows: Approximately 5 gm each of the spleen, liver, kidney and any organ displaying visible lesions were aseptically removed from each bird. Spleen, liver and kidney tissues obtained from the same bird were pooled. Any organ displaying visible lesions was collected and processed separately. In addition, a 10 mm sample of the duodenum, ilea and large intestine tissues with contents were aseptically obtained from each bird and processed individually. In addition, 1 gram of the ceca with contents were collected from each bird and processed similarly.

To culture for Salmonella sp. tissues were placed in a sterile Whirl®pak bag, macerated in a Stomacher blender, and 5 ml of tetrathionate brilliant green Hajna (TBGH) broth added to each bag. The tissue bags were incubated for 24–36 hrs at 42° C., following which a loopful from each culture was streaked onto BGAN. Plates were examined after 36 hours of incubation at 42° C. for characteristic CFU on BGAN agar. After the bag had been incubated for about 48 hours, 1 ml of the TBGH from the bag culture was transferred to a tube of 4 ml of fresh TBGH broth, the tube incubated for 5 days, and then streaked onto BGAN agar. Plates were examined after 36 hours of incubation at 42° C. An agglutination test with group B Salmonella antiserum was performed on at least one colony per plate from all plates to confirm the presence of the wild type challenge strain S. typhimurium F98.

TABLE 1

Experimental design for vaccination with avirulent S. typhimurium and challenge with wild-type S. typhimurium in chickens.

| GROUP | TREATMENT* | AGE AT CHALLENGE | CHALLENGE CULTURE | NUMBER OF BIRDS |
|---|---|---|---|---|
| 1 | Vaccine | 6 weeks | wild-type S. typhimurium | 30 |
| 2 | Distilled water | 6 weeks | wild-type S. typhimurium | 20 |
| 3 | none | N/A | none | 5 |

*Either vaccine or distilled water was administered on day 1 by coarse spray and again on day 14 in the drinking water.

Results:

No clinical reaction to the vaccine was observed after any vaccination. The vaccine strain was isolated from one of thirty birds 8 days after vaccination, but was not recovered from any of the birds thereafter up to the day of challenge. No deaths occurred during the course of the trial.

Culture results for all pre- and post-challenge cloacal swabs are presented in Table 2 below. The vaccine organism was isolated on day 8 post-vaccination from one of the 30 birds; all vaccinated birds were culture negative when sampled again on day 42 post-primary vaccination. Seven days after challenge, wild-type S. typhimurium were cultured from the cloacal swabs of 13% of the vaccinated birds compared to 40% of the non-vaccinated birds receiving distilled water only.

TABLE 2

Number of culture positive cloacal swabs sampled from treated and non treated birds pre- and post-challenge with wild-type S. typhimurium.

| | | PRE-CHALLENGE[1] | | POST-CHALLENGE[2] |
|---|---|---|---|---|
| GROUP | Treatment | Day 8 | Day 42 | Day 49 |
| 1 | S. typhimurium vaccine | 1/30 (3%) | 0/30 (0%) | 4/30 (13%)[3] |
| 2 | Non-treated, challenged controls | 0/20 (0%) | 0/20 (0%) | 8/20 (40%) |
| 3 | Non-treated, non challenged controls | 0/5 (0%) | 0/5 (0%) | 0/5 (0%) |

[1]Number of chickens showing positive culture for S. typhimurium vaccine strain/total number of chickens.
[2]Number of chickens showing positive cultures for wild-type challenge S. typhimurium/total number of chickens.
[3]Significantly different from non-treated, challenged controls using Chi-square test ($P \leq 0.05$).

The vaccinated and non-vaccinated birds also differed in the degree of colonization of the GI tract and the spleen, liver and kidney alternatively (see Table 3). Wild-type S. typhimurium were cultured from pooled organ tissues of 85% of the non-vaccinated control birds compared to 13% of the vaccinated birds ($P \leq 0.05$). A significant reduction in the number of culture positive ileal and large intestine samples was found from vaccinated and non-vaccinated birds ($P \leq 0.05$). A significant reduction was also found in the number of culture positive cecal samples from vaccinated and non-vaccinated birds ($P \leq 0.05$). No differences could be determined between the numbers of culture positive duodenal samples from the vaccinated and non-vaccinated birds.

TABLE 3

Culture of S. typhimurium in broiler age birds vaccinated with avirulent live S. typhimurium challenged with wild-type S. typhimurium.

| | | | CULTURE RESULTS (No. positive/tested (%)) | | | | |
|---|---|---|---|---|---|---|---|
| GROUP | VACCINATION (Day:CFU) | CHALLENGE at 6 weeks (CFU) | Organ Pool | Duodenum | Ilea | Large Intestine | Ceca |
| 1 | Day 1: 3.6 × 10^6 Day 14: 6.8 × 10^6 | 1 × 10^6 | 6/30 (20%)[1] | 1/30 (3%) | 8/30 (27%)[1] | 5/30 (17%)[1] | 7/30 (23%)[1] |
| 2 | None | 1 × 10^6 | 17/20 (85%) | 2/20 (10%) | 12/20 (60%) | 13/20 (65%) | 10/20 (50%) |
| 3 | None | None | 0/5 | 0/5 | 0/5 | 0/5 | 0/5 |

[1]Significantly different from group receiving no vaccination and challenged with wild-type microbe using Chi-square test ($P \leq 0.05$).

The modified live *S. typhimurium* vaccine provided protection to vaccinated birds against artificial challenge with invasive wild-type *S. typhimurium*. This challenge trial showed that birds vaccinated at 1 and 14 days of age with the live *S. typhimurium* vaccine had a statistically significant advantage over control birds. There was a significant reduction in the number of broiler age birds in both treatment groups in internal organ colonization by the wild-type *S. typhimurium* ($P \leq 0.05$). Protection at the gut level was apparent as fewer numbers of vaccinates were culture positive from ileal, large intestine and cecal samples tested than found from these tissues from non-vaccinated birds ($P \leq 0.05$). The duodenum does not appear to be a target tissue for *S. typhimurium* in that only 10% of the non-vaccinated control birds were colonized by the wild-type. In addition, a significant reduction in the number of birds showing positive cloacal culture swabs for the wild-type challenge organism was noted in the vaccine-treated birds as compared to the non-treated birds.

The data from this study demonstrate that *S. typhimurium* vaccine administered to chicks on day one as a coarse spray and in drinking water at day 14 significantly reduces colonization of the GI tract and invasion and colonization of visceral organs by wild-type *S. typhimurium* in broiler age birds.

EXAMPLE 3

This example illustrates the efficacy of spray administration of a live avirulent *S. typhimurium* vaccine in preventing colonization of internal organs following oral challenge with either wild-type *S. enteritidis* or *S. heidelberg*.

antibodies by ELISA. Cloacal swabs were also taken from each bird at this time to culture for the presence of Salmonella sp. At six weeks of age, all birds in Groups 1 and 2 were individually challenged with an oral dose of $1.6 \times 10^8$ CFU in 1.0 ml of wild-type nalidixic acid-resistant *S. heidelberg*. Four days later, all birds were swabbed, euthanized and tissues were recovered and cultured for the wild-type *S. heidelberg* strain as follows. Approximately 10 gm each of the spleen, liver, kidney and any organ displaying visible lesions were aseptically removed from each bird. Spleen, liver and kidney tissues obtained from the same bird were pooled. Any organ displaying visible lesions was collected and processed separately. In addition, a 10 mm sample of the duodenum, ilea and large intestine were aseptically obtained from each bird and processed similarly. In addition, 10 mm sample of the ceca with contents expressed were collected from each bird and processed similarly.

To culture for Salmonella sp., tissues were placed in a sterile whirl pak bag, 25 ml of tetrathionate brilliant green Hajna (TBGH) broth added to each bag and the sample was mascerated in a Stomacher blender. The tissue bags were incubated for 40 hrs at 42° C., following which a 10 μl loopful from each culture was streaked onto brilliant green agar +35 μg/ml novobiocin (BGAN) and xylose-lysine-tergitol 4 agar +100 μg/ml nalidixic acid (XLT4-Nal). Plates were examined after 24 hours of incubation at 42° C. for characteristic colonies on XLT4-Nal and BGAN agar. The enrichment broth cultures were incubated for an additional 24 hours. The cultures corresponding to negative plates were re-streaked onto XLT4-Nal and BGAN, incubated at 42° C. for 24 hours and observed for characteristic colonies. An

TABLE 4

Experimental design for vaccination with *S. typhimurium* vaccine and challenge with *S. heidelberg* or *S. enteritidis* in chickens.

| GROUP | VACCINE | AGE AT VACCINATION | CHALLENGE | AGE AT CHALLENGE | NO. OF BIRDS |
|---|---|---|---|---|---|
| 1 | χ3985 Product Code 19C1.01 | Days 1 & 14 | *S. heidelberg* | 6 weeks | 33 |
| 2 | None | None | *S. heidelberg* | 6 weeks | 20 |
| 3 | None | None | None | None | 10 |
| 4 | χ3985 Product Code 19C1.01 | Days 1 & 14 | *S. enteritidis* | 6 weeks | 33 |
| 5 | None | None | *S. enteritidis* | 6 weeks | 20 |
| 6 | None | None | None | None | 10 |

*S. heidelberg* Study

Sixty-three one-day-old SPF white leghorn chicks (SPAFAS Inc., Storrs, Conn.) were wing banded for use in this trial. At one day of age, 33 birds (Group 1) were vaccinated by coarse spray with $1 \times 10^7$ CFU per dose of vaccine χ3985, Product Code 19C1.01 delivered in approximately 0.35 ml volume per bird using a Preval Power Unit (Precision Valve Corp., Yonkers, N.Y.) spray device. Twenty birds (Group 2) received 0.3 ml per bird of distilled water by coarse spray and served as controls, ten additional birds (Group 3) were held as non-vaccinated, non-challenged controls. Vaccinates and controls were housed separately in Horsfal isolation units.

At two weeks of age, the vaccinates were boosted in the drinking water with $9.6 \times 10^6$ CFU per dose of the same vaccine; for consumption by each bird in 5.1 ml of water. Serum samples were collected prior to challenge from six-week-old birds in Groups 1 and 2 to assess Salmonella agglutination test with Salmonella O group specific (Group B) antiserum was performed on at least one colony per plate from all plates to confirm the presence of the wild-type challenge strain *S. heidelberg*.

Cloacal swabs were collected from each bird of all treatment groups prior to challenge and at the time of sacrifice to monitor for Salmonella sp. Swabs were placed in 5 ml of TBGH broth and incubated for 24–40 hours at 42° C. After about 40 hours, the broth was streaked onto BGAN and incubated at 42° C. An agglutination test with Salmonella O group specific (Group B) antiserum was performed on at least one colony per plate from all plates to confirm the presence of the wild-type challenge strain of *S. heidelberg*.

Results:

No clinical reaction to the vaccine was observed after any vaccinations. No deaths attributed to the vaccine occurred during the course of the trial. One bird in the vaccinated group died from injury on day 49 of the trial. The vaccine was not showed positive cloacal cultures from any bird in Group 1 when sampled on day 42 post-vaccination.

Culture results for all pre- and post-challenge cloacal swabs are presented in Table 5 below. The vaccine organism was not recovered from any of the birds in Group 1 before challenge. Four days after receiving the wild-type challenge organism, 50% of the vaccinated birds showed positive cloacal cultures the wild-type organism while 70% of the non-vaccinated control birds were culture positive. These data show no statistical difference between the two groups in showing positive cloacal cultures for the wild-type organism.

TABLE 5

Number of culture positive cloacal-swab samples from treated and untreated birds pre- and post-challenge with wild-type S. heidelberg.

| TREATMENT | PRE-CHALLENGE[1] (Day 42) | POST-CHALLENGE[2] (Day 46) |
|---|---|---|
| Group 1: S. typhimurium vaccine | 0/33 (0%) | 16/32 (50%)[3] |
| Group 2: Non-treated, challenged controls | 0/20 (0%) | 14/20 (70%)[3] |
| Group 3: Non-treated, non-challenged controls | 0/10 (0%) | 0/10 (0%) |

[1]Number of chickens showing positive culture for S. typhimurium vaccine strain/total number of chickens.
[2]Number of chickens showing positive cultures for wild-type challenge S. heidelberg/total number of chickens.
[3]Significantly different from non-vaccinated non-challenged group using Chi-square test ($P \leq 0.05$).

Groups of vaccinated and non-treated birds were challenged at 6 weeks of age with an oral dose of live wild-type S. heidelberg to assess protection against internal organ tissue invasion and digestive tract colonization (See Table 6). A significant difference was found between the vaccinated and non-vaccinated groups challenged with wild-type S. heidelberg; twenty-five percent of the vaccinated birds challenged with wild-type were culture positive in pooled organ tissues compared to 70% of the non-vaccinated control birds ($P \leq 0.05$). A significant reduction in the number of culture positive digestive tract pooled samples was found from vaccinated compared to non-vaccinated birds ($P \leq 0.05$). No differences in the number of culture positive cecal samples were seen between the vaccinated and non-vaccinated birds. Non-treated, non-challenged control birds were free of Salmonella Sp.

TABLE 6

Protection of broiler age birds vaccinated with live avirulent S. typhimurium and challenged with wild-type S. heidelberg

| GROUP TREATMENT | ORGAN POOL | DIGESTIVE TRACT POOL | CECA |
|---|---|---|---|
| 1 Vaccine + challenge | 8/32 (25%)[1] | 10/32 (31%)[1] | 21/32 (66%) |
| 2 Non-vaccinated challenged controls | 14/20 (70%) | 17/20 (85%) | 17/20 (85%) |

TABLE 6-continued

Protection of broiler age birds vaccinated with live avirulent S. typhimurium and challenged with wild-type S. heidelberg

| GROUP TREATMENT | ORGAN POOL | DIGESTIVE TRACT POOL | CECA |
|---|---|---|---|
| 3 Non-vaccinated, non-challenged controls | 0/10 (0%) | 0/10 (0%) | 0/10 (0%) |

[1]Significantly different from non-vaccinated, challenged group using Chi-square test ($P \leq 0.05$).

S. enteritidis Study:

Table 4 shows the experimental design of the S. enteritidis efficacy study.

Sixty-three one-day-old SPF white leghorn chicks (SPAFAS Inc., Storrs, Conn.) were wing banded for use in this trial. At day-of-age, 33 birds (Group 4) were vaccinated by coarse spray with $1 \times 10^7$ CFU per dose of χ3985, Product Code 19C1.01 vaccine carried in approximately 0.35 ml volume per bird using a Preval Power Unit spray device (Precision Valve Corp., Yonkers, N.Y.). Twenty birds (Group 5) received 0.3 ml per bird of distilled water by coarse spray and served as controls, ten additional birds (Group 6) were held as non-vaccinated, non-challenged controls. Vaccinates and controls were housed separately in Horsfal isolation units.

At two weeks of age, the vaccinates were boosted in the drinking water with $9.6 \times 10^6$ CFU per dose of the same vaccine for consumption by each bird in 5.1 ml of water. Serum samples were collected prior to challenge from 6-week-old birds in Groups 4, 5 and 6 to assess Salmonella antibodies by ELISA. Cloacal swabs were also taken from each bird at this time to culture for the presence of Salmonella sp. At six weeks of age, all birds in Groups 4 and 5 were individually challenged with an oral dose of $4.5 \times 10^7$ CFU in 1.0 ml of wild-type nalidixic acid-resistant S. enteritidis. Seven days later, all birds were swabbed, euthanized and cultured for the wild-type S. enteritidis strain by the method described above in the S. heidelberg efficacy study, except that the agglutination tests were run with Salmonella O group specific (Group D) antiserum rather than Group B antiserum.

Results

No clinical reaction to the vaccine was observed after any vaccinations. No deaths attributed to the vaccine occurred during the course of the trial. One bird in the vaccine-treated group died, presumably from injury received after heart puncture in an effort to collect blood for serum antibody evaluation.

Culture results for all pre- and post-challenge cloacal swabs are presented in Table 7 below. The vaccine organism was not recovered from any of the birds in Group 4 before challenge. Seven days after receiving the wild-type challenge organism, 41% of the vaccinated birds showed positive cloacal cultures for the wild-type organism while 63% of the non-vaccinated control birds were culture positive. These data show no statistical difference between the two groups in positive cloacal cultures for the wild-type organism.

TABLE 7

Number of culture positive cloacal swabs samples from vaccinated and non-vaccinated birds pre- and post-challenge with wild-type S enteritidis.

| GROUP | TREATMENT | PRE-CHALLENGE[1] (Day 42) | POST-CHALLENGE[2] (Day 49) |
|---|---|---|---|
| 4 | Vaccine + challenge | 0/33 (0%) | 13/32 (41%)[3] |
| 5 | Non-vaccinated, challenged controls | 0/20 (0%) | 12/19 (63%)[3] |
| 6 | Non-vaccinated, non-challenged controls | 0/10 (0%) | 0/10 (0%) |

[1]Number of chickens showing positive culture for *S. typhimurium* vaccine strain/total number of chickens.
[2]Number of chickens showing positive cultures for wild-type challenge *S. typhimurium*/total number of chickens.
[3]Significantly different from non-vaccinated, non-challenged controls using Chi-square test ($P \leq 0.05$).

The vaccinated and non-vaccinated birds also differed in the degree of colonization of the GI tract and the spleen, liver and kidney collectively as shown in Table 8. A significant difference was found between the vaccinated and non-vaccinated groups challenged with wild-type *S. enteritidis;* nine percent of the vaccinated birds challenged with wild-type were culture positive in pooled internal organ tissues compared to 58% of the non-vaccinated control birds ($P \leq 0.05$). A significant reduction in the number of culture positive digestive tract pooled samples was found from vaccinated and non-vaccinated birds ($P \leq 0.05$). No differences in the number of culture positive cecal samples were seen between the vaccinated and non-vaccinated birds. Non-treated, non-challenged control birds were free of Salmonella sp.

TABLE 8

Protection of broiler age birds vaccinated with a modified live *S. typhimurium* vaccine after oral challenge with wild-type *S. enteritidis*.

| GROUP | TREATMENT | ORGAN POOL | DIGESTIVE TRACT POOL | CECA |
|---|---|---|---|---|
| 4 | Vaccine + challenge | 3/32 (9%)[1] | 4/32 (13%)[1] | 16/32 (50%) |
| 5 | Non-vaccinated, challenged controls | 11/19 (58%) | 7/19 (37%) | 11/19 (58%) |
| 6 | Non-vaccinated, Non-challenged controls | 0/10 (0%) | 0/10 (0%) | 0/10 (0%) |

[1]Significantly different from non-vaccinated challenged controls using Chi-square test ($P \leq 0.05$).

Serum samples were screened for IgG antibody to *S. typhimurium* lipopolysaccharide (LPS) by ELISA. Samples were diluted 1:100 and added to duplicate wells coated with commercially prepared *S. typhimurium* LPS. HRP-conjugated rabbit anti-chicken IgG at 1:30,000 was used for detection. Of the birds vaccinated with *S. typhimurium* vaccine, 52% developed a strong response to the vaccine with $OD_490$ measurements greater than 0.3; nine percent responded positively in the mid-range of 0.2–0.3 and 39% measured in the low-range of 0.05–0.1. Sera from control birds averaged $OD_{490}$ measurements of 0.005±0.009, well below all measurements derived from sera from vaccinated birds.

Conclusion:

Day-of-hatch, spray vaccination with the live avirulent *S. typhimurium* vaccine, $\chi 3985$, Product Code 19C1.01, followed by oral administration of the vaccine in the drinking water at day 14 did not produce any adverse reaction in chickens. The vaccine strain was not recovered from cloacal swabs of spray vaccinated birds when sampled at 6 weeks of age or just prior to challenge with the wild-type *S. enteritidis* or *S. heidelberg* organisms. All vaccinated birds that were tested mounted a serologic response when exposed to the *S. typhimurium* vaccine as compared to non-vaccinated birds.

The data generated from this trial demonstrate that the *S. typhimurium* vaccine provided significant protection to reduce the level of colonization of internal organs by either *Salmonella heidelberg* or *S. enteritidis*. Although no differences were seen in the level of colonization by the wild-type challenge strains in the ceca of vaccinated compared to non-vaccinated birds, significant protection from *S. heidelberg* or *S. enteritidis* colonization of the digestive tract was conferred by vaccination.

EXAMPLE 4

This shows the efficacy of spray vaccination using a live avirulent *S. typhimurium* vaccine in protecting broiler age birds against internal organ colonization after challenge with wild-type *S. enteritidis*.

Fifty-five one-day-old SPF white leghorn chicks (HyVac, Adel, IA) were wing banded for use in this trial. At day-of-age, 30 birds (Group 1) were vaccinated by coarse spray with approximately $1 \times 10^7$ CFU per dose of $\chi 3985$, Product Code 19C1.01 vaccine (produced by Maine Biological Laboratories, Inc., Waterville, Me.), carried in approximately 0.3 ml volume per bird using a Preval Power Unit spray device (Precision Valve Corp., Yonkers, N.Y.). Twenty birds (Group 2) received 0.3 ml per bird of distilled water by coarse spray and served as controls, five additional birds (Group 3) were held as contemporary controls. Vaccinates and controls were housed separately in Horsfal isolation units.

TABLE 9

Experimental design for vaccination with *S. typhimurium* vaccine and challenged with *Salmonella enteritidis*.

| GROUP | VACCINE | AGE AT VACCINATION | CHALLENGE | AGE AT CHALLENGE | NO. OF BIRDS |
|---|---|---|---|---|---|
| 1 | Chi3985, Product Code 19C1.01 | Days 1 & 14 | *S. enteritidis* | 6 weeks | 30 |

TABLE 9-continued

Experimental design for vaccination with *S. typhimurium* vaccine and challenged with *Salmonella enteritidis*.

| GROUP | VACCINE | AGE AT VACCINATION | CHALLENGE | AGE AT CHALLENGE | NO. OF BIRDS |
|---|---|---|---|---|---|
| 2 | None | None | S. enteritidis | 6 weeks | 20 |
| 3 | None | None | None | N/A | 5 |

At two weeks of age, the vaccinates were boosted in the drinking water with approximately $1 \times 10^7$ CFU per dose of the same vaccine (one dose in 15 ml of water per bird). At six weeks of age all birds in the vaccine-treated and control groups were individually challenged with an oral dose of $4 \times 10^7$ CFU in 0.5 ml of wild-type *S. enteritidis*. Cloacal swabs were also collected 5 days post challenge from each bird to assess the number of wild-type cloacal swabs. All birds were euthanized 5 days post challenge, necropsied and tissue samples cultured for the wild type S. enteritidis as described in Example 2.

Results:

No clinical reaction to the vaccine was observed during the vaccination period. No deaths occurred in all treatment groups during the course of the trial.

Groups of vaccinated and non-treated birds were challenged at six weeks of age with an oral dose of live wild-type *S. enteritidis* to assess protection against internal organ tissue invasion and GI tract colonization. (See Table 10). A significant difference was found between the vaccinated and non-vaccinated groups challenged with wild-type *S. enteritidis*; ninety-five percent of the non-vaccinated control birds challenged with wild-type were culture positive in pooled organ tissues after challenge compared to 20% of the vaccinated birds ($P \leq 0.01$). A significant reduction in the number of culture positive duodenal samples was found within the vaccine-treated group and control group ($P \leq 0.01$). No differences were found between the number of S. enteritidis culture positive ileal, large intestine or cecal samples from vaccinated and non-vaccinated birds.

Eighty-six percent of the vaccine treated birds showed positive cloacal cultures for the wild-type challenge organism compared to 100% of the birds in the non-vaccinated control group.

Conclusion:

Day of hatch spray vaccination with the live χ3985 Product Code 19C1.01 vaccine, followed by oral administration of the vaccine in the drinking water at day 14 did not produce any adverse reaction in chickens.

Although protection from wild-type colonization was not apparent in the digestive tract and cecal samples of vaccinated birds, significant protection against internal organ colonization by the wild-type *S. enteritidis* was demonstrated in the internal organs of vaccine-treated, challenged birds compared to non-vaccinated, challenged birds.

EXAMPLE 5

This example illustrates that spray vaccination of chicks with modified live *S. typhimurium* vaccine was safe and efficacious in reducing Salmonella contamination under field conditions of normal large-scale commercial poultry production.

Purpose:

The purpose of this trial was to evaluate the safety and potential of the χ3985, Product Code 19C1.01 vaccine to reduce Salmonella contamination under normal large scale commercial poultry production conditions. The safety of the vaccine was monitored by measuring the ability of the product to spread and the survival of the chickens during the grow-out period. The efficacy of the product was monitored by bacteriological analyses of post-chill carcass rinses after processing, average weight and the percent condemnations at processing.

Materials and Methods:

Three geographically distinct farms with paired houses were chosen such that each poultry house accommodated a minimum of 16,000 birds. This allowed a triple-replicate trial utilizing more than 115,000 birds consisting of control birds and birds treated with the modified live *S. typhimurium* vaccine. An effort was made to identify trial poultry farms that had a known background history of persistent Salmonella contamination. Table 11 identifies the sites and study parameters of the three trials.

TABLE 10

Protection of broiler age birds vaccinated with a modified live *S. typhimurium* vaccine after oral challenge with wild-type *S. enteritidis*

| GROUP | TREATMENT | ORGAN POOL | DUODENUM | ILEA | LARGE INTESTINE | DIGESTIVE TRACT (Pooled data) | CECA |
|---|---|---|---|---|---|---|---|
| 1 | Vaccine | 6/30 (20%)[1] | 2/30 (7%)[1] | 26/30 (87%) | 27/30 (90%) | 20/30 (67%) | 29/30 (97%) |
| 2 | Controls | 21/22 (95%) | 12/22 (55%) | 15/22 (68%) | 22/22 (100%) | 22/22 (100%) | 22/22 (100%) |
| 3 | Isolated controls | 0/5 (0%) | 0/5 (0%) | 0/5 (0%) | 0/5 (0%) | 0/5 (0%) | 0/5 (0%) |

[1]Significantly different from non-vaccinated, challenged control groups using Chi Square Test ($\alpha = 0.01$).

TABLE 11

Description of vaccine field safety trials

| FIELD TRIAL SITE | VACCINE SERIAL USED | NO. OF CHICKENS | | TIME OF VACCINATION (Days after hatching) | | DURATION OF TRIAL (DAYS) |
|---|---|---|---|---|---|---|
| | | VACCINATED | CONTROL | FIRST | BOOSTER | |
| 1 | 7002 | 21,000 | 21,000 | 1 | 14 | 48 |
| 2 | 7003 | 20,500 | 20,500 | 1 | 17 | 42 |
| 3 | 7004 | 16,000 | 16,000 | 1 | 15 | 64 |

Production of Prelicensing Serials:

The modified live χ3985, Product Code 19C1.01 vaccine prelicensing serials were manufactured following the Outline of Production filed and approved March 20, 1995.

Trial Procedure:

At all farm sites, the normal commercial vaccination, feeding and watering regimens of that particular poultry establishment were followed. Hatchlings received Marek's vaccine either in ovo or at day of hatch and Newcastle/bronchitis vaccine by spray at day of hatch. A booster bronchitis vaccination was administered in both houses on each farm site on day 16–18 of the study.

Application Procedures for the *S. typhimurium* Vaccine:

1. Spray application at day of age:

A portable spray box apparatus (supplied and operated by Merial Select, Atlanta, GA) was set up in the hatchery so that incoming boxes of birds were vaccinated prior to setting the chicks out on the floor of the house. Vaccine was supplied as a lyophilized formulation in a glass vial. The vaccine was mixed into clean, non-chlorinated water according to the package instructions. The spray equipment was pre-calibrated manually to deliver approximately 700 ml to 1 liter over 10,000 chicks under a pressure of 1 bar (15 psi) using 4 coarse anvil fantail spray nozzles to deliver 50–100 micron sized droplets. This delivered approximately 0.07–0.1 ml per chick.

2. Drinking water application at two weeks of age:

Two-week old birds were deprived of drinking water for a period of two to four hours before allowing birds in the treated house on each farm access to the vaccine water. The Merial Select Bag Boost system was implemented for calibrated delivery of the vaccine. The required quantity of the *S. typhimurium* vaccine was mixed according to the package instructions to a final volume of diluent sufficient to administer one dose per bird over a two hour period through all house water lines. This vaccine water was the bird's only source of water over this two-hour period to ensure that all birds had the opportunity to drink sufficient vaccine. The well water used in the houses on all farms was tested prior to water vaccination and was found to be negative for chlorine residue and within a pH range of 6.0–7.0.

Sampling and enrichment culture procedures during the trial:

To monitor the presence of indigenous wild-type Salmonella spp. in the environment and in the chick, base-line samples of meconia from chick papers were collected in the hatchery, while litter drag swabs, feed and water were collected in the houses for bacteriological analysis as described below. Drag swabs of the litter, feed and water samples were collected periodically throughout the trials at each test site.

1. Chick papers and swabs:

A random sample of 12–18 chick papers and swabs representative of each breeder flock was collected from individual chick transport boxes before administering the vaccine. Each chick paper selected containing meconia was placed in individual plastic bags, which were sealed and labeled. Sterile gauze pads wetted with sterile skim milk were used to swab additional chick papers, then placed in plastic Whirl® Pak bags, sealed and labeled. All samples were immediately transported on ice packs to the laboratory for analysis of Salmonella spp. to determine a base-line level of contamination of incoming chicks.

2. Feed and water samples:

Before the start of the study, a 40 g sample of feed was taken from the internal bin auger inflow stream from each farm. These samples were placed in Whirl® Pak bags and labeled. In addition, 100 ml of water was collected at the source after the filter and 100 ml of water collected from the nipple drinker from each house. The collected water was immediately analyzed for chlorine residue and range of pH. Samples of feed and water were collected every two weeks throughout the trial period for each farm, labeled and transported on ice packs to the laboratory for bacteriological analysis.

3. Dray swab samples of house litter:

Before the start of each trial, drag swab samples of the litter were collected from each house on each farm to determine base-line levels of Salmonella contamination. Additional drag swab samples of each house on each farm were collected every two weeks throughout the trial period. Drag swab assemblies were constructed following the National Poultry Improvement Plan and Auxiliary Provisions (National Poultry Improvement Plan and Auxiliary Provisions manual. United States Department of Agriculture, Animal and Plant Health Inspection Service (APHIS 92-55-017), April 1993). The bags were sealed, labeled and transported on ice packs to the laboratory for bacteriological analyses.

4. Culture procedures:

Buffered peptone water (International Bioproducts Inc., Redman, Wash.; Difco Inc., Detroit, Mich.) was used to pre-enrich feed, water, chick swabs, chick papers and drag swabs and served as the rinse to assess the bacterial load on carcasses. Tetrathionate brilliant green-Hajna broth (Northeast Laboratories Inc., Waterville, Me.) was used as selective media for enrichment of Salmonella sp. or the vaccine. Tetrathionate brilliant green agar supplemented with 35 pg novobiocin/ml (Sigma, St. Louis, Mont.) was used to identify characteristic growth of Salmonella sp. or the vaccine. Confirmation of Salmonella was accomplished following the procedures outlined in the FSIS Sample Collection Guidelines and Procedure for Isolation and Identification of Salmonella from Raw Meat and Poultry Products. All positive cultures were sent to National Veterinary Services Laboratory (Ames, Iowa) for serotyping.

5. Bacteriological assessment of whole carcasses:

Fifty carcasses were randomly selected post-chill after processing from each house. The FSIS Sample Collection Guidelines and Procedure for Isolation and Identification of Salmonella from Raw Meat and Poultry Products (Food Safety Inspection Service Sample Collection Guidelines and Procedure for Isolation and Identification of Salmonella from Raw Meat and Poultry Products, Federal Register Vol. 61, No. 144, 7/25/96, page 38923), was followed to collect whole carcass rinses and to assess the presence or absence of Salmonella sp. and/or vaccine residues. In addition, PCR (BACS System, Qaulicom, Wilmington, Del.) was used to verify samples that were positive for agglutination by antisera to specific Salmonella O-antigen groups (Difco Inc., Detroit, Mich.), but where pure cultures could not be obtained.

Statistical Methods:

The $\chi$-Square test was used to compare parametric results between vaccine-treated and control houses.

Results and Discussion:

Trial at Site No. 1:

1. Analyses of base-line samples:

Analyses of base-line samples consisting of chick papers and paper swabs, water, feed and drag swabs of the house litter collected prior to the start of the trial revealed that the feed from the control house was positive for *Salmonella mbandaka* and chicks from two of three breeder flocks showed positive cloacal cultures for *Salmonella heidelberg*. Chicks from one of the breeder flocks showed positive cloacal cultures for organisms suspected to be of O-antigen group $C_3$, however a pure isolate could not be recovered. No other Salmonella sp. or vaccine organisms could be recovered from feed, water or from drag swabs of the litter from either house on the farm for the remainder of the 6-week grow-out period of the trial.

2. Livability:

Livability data were collected weekly by the grower for each house on the farm. Table 12 shows the numbers of birds that expired during the grow-out period of the trial. No difference was seen in the loss of birds between the control and treated house where the percent total loss for both houses was 2.8%, respectively. The average percent mortality for a period coinciding with the trial for the region of the country in which Site #1 was located was 4.4–4.7% (*The Poultry Informed Professional*, Department of Avian Medicine, University of Georgia, Athens, Ga., January, 1998).

TABLE 12

Mortality of birds during the grow-out period for Site #1 trial.

|  | CONTROL | TREATED |
|---|---|---|
| 1st Week | 205 | 210 |
| 2nd Week | 117 | 87 |
| 3rd Week | 57 | 55 |
| 4th Week | 62 | 63 |
| 5th Week | 74 | 81 |
| 6th Week | 81 | 87 |
| Total mortality headcount | 596 | 583[1] |
| Percent total | 2.8% | 2.8% |

[1]No significant difference was found using Chi-square test ($P \leq 0.05$)

The historical livability percentile for Site #1 ranged from 95.5 to 99.6 in 1996–1997. The livability percentile of 97.2 for both the control and treated birds was within this range. Based on these data, the vaccine did not have any adverse effect on the livability of the birds.

3. FSIS Inspector's condemnation report at processing:

The USDA Inspector's condemnation report for each house is presented in Table 13. The Inspector's report indicated an increase of airsacculitis and inflammatory process (IP) in the carcasses from the treated house over the control house. Average values for the region were obtained from *The Poultry Informed Professional*—for a week during the trial.

TABLE 13

Percent condemnations at processing for Site #1 trial.

| CONDEMNATION CAUSE | CONTROLS | TREATED | AVERAGE % FOR REGION |
|---|---|---|---|
| Leukosis | 0.02 | 0.02 | 0.03 |
| Septicemia/Toxemia | 0.25 | 0.28 | 0.35 |
| Tumors | 0.28 | 0.15 | N/A[1] |
| Airsacculitis | 0.14 | 0.51 | 0.17 |
| Synovitis | 0 | 0 | N/A |
| Inflammatory process | 0.64 | 2.06 | 0.14 |
| Overscald | 0 | 0 | N/A |
| Bruises | <0.01 | <0.01 | 0.02 |
| Tuberculosis | 0 | 0 | N/A |
| Cadavers | <0.01 | <0.01 | N/A |
| Contaminated | <0.01 | <0.01 | N/A |
| Dead on arrival | 0.3 | 0.24 | N/A |
| Total condemnations | 1.33 | 3.02[2] |  |

[1]N/A indicates data not available.
[2]Significantly different from control group using Chi-square test ($P \leq 0.05$)

The historical data provided by the collaborator shows that this test farm had experienced cyclic episodes of respiratory disease in the past two years as airsacculitis percentiles had been elevated during the winter months. The flock that was on the farm prior to this vaccinated test flock showed airsacculitis percentiles of 1.71, compared to 0.51 for the birds in the treated house from this trial. There are no documented cases of Salmonella spp. causing airsacculitis or inflammatory process. In addition, the carcass inspection process was not blinded as the USDA Inspector in Charge required identification of the treated birds. Airsacculitis and IP percentiles were not different between controls and vaccine-treated birds in two subsequent trials described in this report. Based on these reasons, an assessment cannot be made for the cause of these conditions as attributed to use of the vaccine product.

4. Evaluation of the carcass weight at processing.

The average weight of the bird at processing is an indicator of performance of the bird during grow-out period. An examination of eight grow-out cycles for Site #1 showed average bird weights ranging from 4.36 to 4.79 lbs for birds up to 49 days of age; the treated bird weights fell within this range averaging 4.84 lbs compared to 4.85 lbs for control birds at 48 days of age. Based on these average weight data, the vaccine did not affect the ability of the birds to maintain a level of performance expected by the producer.

5. Carcass rinse evaluation.

The results of carcass rinse evaluation are shown in Table 14. The number of Salmonella positive samples as identified by PCR and O-antigen antisera agglutination from carcass rinses was significantly less in the treatment group than that found in the control group ($p \leq 0.05$). Neither the modified live *S. typhimurium* organisms nor any indigenous Salmonella sp. was identified from the 50 carcass rinse samples from the treated group analyzed in the laboratory. However, eight percent of the rinse samples taken from the 50 carcasses from the control group were positive for Group C Salmonella indicating that the vaccine was efficacious in eliminating indigenous Salmonella from the meat product.

TABLE 14

Site #1 carcass rinse evaluation.

| GROUP | NUMBER OF POSITIVE SAMPLES |
|---|---|
| Control | 4/50 (8%) |
| Treated | 0/50 (0%)[1] |

[1]Significantly different from control group using Chi-square test (P ≤ 0.05)

Trial at Site No. 2:

1. Analyses of base-line samples.

Analyses of base-line samples collected revealed that the feed from the control house and the meconia from chick papers contained organisms suspected to be of O-antigen group $C_3$, however pure isolates were not recovered. No other Salmonella sp. or vaccine organism could be identified from feed, water or from drag swabs of the litter from either house on the farm for the remainder of the 6-week grow-out period of the trial.

2. Livability.

Livability data were collected periodically for each house on the farm. Table 15 shows the mortality data during the grow-out period of the trial. Fewer birds expired in the control house than the treated house during the first week of the trial. No differences in the number of birds that expired between the groups were observed after the first week of the trial. The average percent mortality for a week during the trial period was 5.0–6.2 for the region of the country in which the trial took place (*The Poultry Informed Professional*, February 1998). The mortality in each house fell below the regional average for this period.

TABLE 15

Mortality of birds during the grow-out period for the Site #2 trial.

|  | CONTROLS | TREATED |
|---|---|---|
| Day 7 | 236 | 363 |
| Day 14 | 88 | 73 |
| Day 30 | 281 | 306 |
| Day 35 | 64 | 60 |
| Day 42 | 82 | 78 |
| Total mortality headcount | 751 | 880[1] |
| Percent total | 3.7 | 4.3 |

[1]Significantly different from control group using Chi-square test (P ≤ 0.05)

The 0.6 percent difference in mortality between the treated and control birds in the first week is within the expected deviation observed for hatchlings. There was no difference in the numbers of mortality headcount after the first week through the end of the trial. This difference in first week mortality was not observed in two of the three trials conducted with the vaccine product. Factors that can affect survival of hatchlings can include variations of the age of the breeder chickens, the quality of the breeder and hatchery management and extended exposure to temperatures less than 85° F. Survival percentiles for 40–42 day old birds previously raised on this test farm during the same year as the trial ranged from 94.7 to 97.5. The survival percentile for the control and treated birds fell within this range with 96.3 and 95.7 percent, respectively.

3. FSIS Inspector's condemnation report at processing.

The USDA Inspector's condemnation report for each house is presented in Table 16. Data for the average % for the same region of the country for site #2 was obtained from the Poultry Informed Professional, February, 1998. No difference in the number of birds condemned in the control and treated groups was observed in this trial.

TABLE 16

Percent condemnations at Site #2 trial.

| CONDEMNATION CAUSE | CONTROL | TREATED | AVERAGE % FOR SAME REGION AS SITE #2 |
|---|---|---|---|
| Leukosis | <0.01 | <0.01 | 0.01 |
| Septicemia/Toxemia | 0.21 | 0.13 | 0.41 |
| Tumors | 0.07 | 0.02 | N/A[1] |
| Airsacculitis | 0.25 | 0.18 | 0.39 |
| Ascites | 0.11 | 0.15 | N/A |
| Inflammatory process | 0.43 | 0.58 | 0.45 |
| Overscald | 0.05 | 0.01 | N/A |
| Bruises | 0.03 | 0.04 | 0.08 |
| Tuberculosis | 0 | 0 | N/A |
| Cadavers | 0.03 | 0.04 | N/A |
| Contaminated | 0.05 | 0.05 | N/A |
| Dead on arrival | 0.21 | 0.21 | N/A |
| Total condemnations | 1.44 | 1.41[2] |  |

[1]N/A indicates data not available.
[2]Not significantly different from control group using Chi-square test at the P ≤ 0.05 level.

4. Evaluation of carcass weight at processing.

The average weight of birds during nine grow-out cycles on Site #2 ranged from 3.35 to 3.93 lbs; the treated bird weights fell within this range averaging 3.7 lbs at 42 days of age. The weight of the birds from the treated house were 6.1% lower than the control birds' average weight at processing. However, the weight of the treated birds cannot be compared to the control group as two of the four water lines in the treated house were discovered to be blocked during the fourth week of the trial. It was the opinion of the Broiler Manager that this weight difference may be partially or wholly due to this problem.

5. Carcass rinse evaluation.

Table 17 shows Salmonella positive samples identified from carcass rinses in treatment group. No vaccine organisms or wild-type Salmonella sp. were identified in any of the 100 rinse samples from either group.

TABLE 17

Site #2 carcass rinse evaluation.

| GROUP | NUMBER OF POSITIVE SAMPLES |
|---|---|
| Controls | 0/50 |
| Treated | 0/50 |

Trial at Site #3:

1. Analyses of base-line samples.

Analyses of base-line samples collected revealed that the litter drag swabs taken from the control house contained organisms suspected to be of O-antigen Group $C_3$, however a pure isolate could not be recovered. The chicks originating from two breeder flocks were culture negative for indigenous Salmonella spp. No other Salmonella spp. or vaccine organism could be identified from feed, water or from drag swabs of the litter from either house on the farm for the remainder of the 64-day grow-out period of the trial.

2. Livability.

Livability data were collected weekly for each house. Table 18 shows the mortality data collected during the grow-out period of the trial.

TABLE 18

Mortality of birds during the grow-out period for the Site #3 trial.

|  | CONTROLS | TREATED |
|---|---|---|
| 1st Week | 293 | 328 |
| 2nd Week | 151 | 176 |
| 3rd Week | 76 | 114 |
| 4th Week | 60 | 70 |
| 5th Week | 86 | 68 |
| 6th Week | 103 | 97 |
| 7th Week | 109 | 84 |
| 8th Week | 97 | 118 |
| 9th Week | 105 | 119 |
| Total mortality headcount | 1080 | 1174[1] |
| Percent total | 6.8 | 7.3 |

[1]Significantly different from control group using Chi-square test (P ≦ 0.05)

It should be noted that a difference in mortality between the control and treated groups was due to only a five bird deviation. It is our speculation that a standard deviation would exist due to the significant number of errors discovered on the daily mortality charts. Therefore, given the uncertainty of the actual headcounts one could expect a margin of error as low as 0.03% to contribute significantly to the final statistical differences. However, when the final survival values were compared for the previous six-months grow-out cycles for this site for the year of the trial, percentiles ranged from 90 to 95. The livability percentiles for control and treated birds from this trial were 93.2 and 92.7, respectively, and fell within this range.

3. FSIS Inspector's condemnation report at processing.

Condemnation data for the two treatment groups from Site #3 carcasses was inadvertently combined by the USDA Inspectors. The Inspector's condemnation report for both houses is presented in Table 19. Averages for the region including Site #3 are based on a 6-week old broiler for the same period as the trial (*The Poultry Informed Professional*, April, 1998). The condemnation rates for the present trial in the five categories specified in Table 19 are the same or lower than those for the region of the country in which Site #3 was located as measured for a week during the trial period. The treatment of the birds with the vaccine did not adversely affect the condemnation percentiles in any category inspected.

TABLE 19

Percent condemnations at processing for Site #3.

| CONDEMNATION CAUSE | COMBINED DATA (%) FOR TREATED AND CONTROL BIRDS | AVERAGE (%) FOR SAME REGION |
|---|---|---|
| Leukosis | <0.01 | 0.04 |
| Septicemia/Toxemia | 0.26 | 0.26 |
| Tumors | 0.01 | N/A[1] |
| Airsacculitis | 0.16 | 0.3 |
| Ascites | 0.05 | N/A |
| Inflammatory process | 0.1 | 0.3 |
| Overscald | 0 | N/A |
| Bruises | 0 | 0.01 |
| Tuberculosis | 0 | N/A |
| Cadavers | 0.04 | N/A |
| Contaminated | <0.01 | N/A |
| Dead on arrival | 0.3 | N/A |
| Total condemnations | 0.92 |  |

[1]N/A indicates data not available.

4. Evaluation of carcass weight at processing.

An examination of three previous grow-out cycles for Site #3 showed birds' weights ranging from 6.67 to 7.2 lbs. For this study, the average weight of the birds at processing was 7.33 lbs. It should be noted that although this producer has experienced over the past year a decline in the quality of the chicks received from the breeder (as noted by the high mortality during the first two weeks of the trial), the excellent performance and final heavy weight of the birds at processing for this trial was unexpected. Based on these average weight data, the vaccine did not affect the ability of the birds to maintain a level of performance expected by the producer.

5. Carcass rinse evaluation.

Table 20 shows the results of the analyses of carcass rinse samples for each group. Neither the modified live *S. typhimurium* organisms nor any indigenous Salmonella sp. was recovered from the 50 treated house carcass rinse samples. However, twelve percent of the rinse samples taken from the 50 carcasses from the control group were PCR and culture positive for *S. heidelberg* and *S. hadar*.

TABLE 20

Site #3 carcass rinse evaluation.

| GROUP | NUMBER OF POSITIVE SAMPLES |
|---|---|
| Control | 6/50 (12%)[1] |
| Treated | 0/50 (0%)[2] |

[1]Cultures were identified as either *S. heidelberg* or *S. hadar*.
[2]Significantly different from control group using Chi-square test (P ≦ 0.05).

Conclusions:

Spray vaccination with the live *S. typhimurium* vaccine, χ3985, Product Code 19C1.01, was found to be safe for use in commercial broiler chickens. The birds maintained a level of health and performance expected by the producer after exposure to the vaccine product. The immediate test environment was found to be free of vaccine residue. The vaccine was found to be efficacious in that its use resulted in complete elimination of indigenous Salmonella sp. on the carcasses from the treated groups compared to the control groups in two of three trials. These results confirm that the vaccine was found to be both safe and efficacious in trials conducted in cooperation with three commercial poultry operations.

All references cited in this specification are hereby incorporated by reference. The discussion of the references herein is intended merely to summarize the assertions made by their authors and no admission is made that any reference constitutes prior art. Applicants reserve the right to challenge the accuracy and pertinency of the cited references.

In view of the above, it will be seen that the several advantages of the invention are achieved and other advantageous results obtained.

As various changes could be made in the above methods and compositions without departing from the scope of the invention, it is intended that all matter contained in the above description and shown in the accompanying drawings shall be interpreted as illustrative and not in a limiting sense.

What is claimed is:

1. A method of vaccinating a domestic bird comprising administering by whole-body spray, an effective amount of a vaccine comprising a live avirulent derivative of an enteropathogenic bacteria to the bird, wherein said enteropathogenic bacteria is other than one that causes respiratory disease in birds.

2. The method according to claim 1 wherein the enteropathogenic bacteria is a Salmonella.

3. The method according to claim 2 wherein the spray is administered in a dose of from about $10^5$ to about $10^8$ colony forming units of the live avirulent derivative of a pathogenic bacteria.

4. The method according to claim 3 wherein the Salmonella is *S. typhimurium*.

5. The method according to claim 4 wherein the *S. typhimurium* is χ3985.

6. The method according to claim 3 wherein the bird is 3 weeks of age or less.

7. The method according to claim 6 wherein the bird is less than one day of age.

8. The method according to claim 7 wherein the bird is a chicken.

9. The method according to claim 7 wherein the administering by spray is followed by administering at least one booster dose of the vaccine.

10. The method according to claim 9 wherein the booster dose of the vaccine is administered in the drinking water.

11. The method according to claim 10 wherein a booster dose is administered 14 days after the administering by spray.

12. The method according to claim 1 wherein the spray is a coarse spray of droplets having diameters in the range of from 50 microns to 150 microns.

13. A method of reducing microbial contamination of poultry comprising immunizing the poultry against a microbial contaminant by whole-body spray administration of a vaccine comprising a live avirulent derivative of an enteropathogenic bacteria, wherein said enteropathogenic bacteria is other than one that causes respiratory disease in birds.

14. The method according to claim 13 wherein the enteropathogenic bacteria is a Salmonella.

15. The method according to claim 14 wherein the spray is administered in a dose of from about $10^5$ to about $10^8$ colony forming units of the live avirulent derivative of a pathogenic bacteria.

16. The method according to claim 15 wherein the Salmonella is a *S. typhimurium*.

17. The method according to claim 18 wherein the *S. typhimurium* is χ3985.

18. The method according to claim 16 wherein the poultry are less than 104 weeks of age.

19. The method according to claim 16 wherein the poultry are 3 weeks of age or less.

20. The method according to claim 19 wherein the poultry are less than one day of age.

21. The method according to claim 20 wherein the poultry are chickens.

22. The method according to claim 18 wherein the spray administration is followed by administration of at least one booster dose of the vaccine in the drinking water.

23. The method according to claim 22 wherein a booster dose is administered 14 days after the spray administration.

24. The method according to claim 13 wherein the spray administration comprises spraying droplets having diameters in the range of from 50 microns to 150 microns.

* * * * *

UNITED STATES PATENT AND TRADEMARK OFFICE
CERTIFICATE OF CORRECTION

PATENT NO. : 6,713,073 B1
DATED : March 30, 2004
INVENTOR(S) : Sandra M. Aehle

It is certified that error appears in the above-identified patent and that said Letters Patent is hereby corrected as shown below:

Column 30,
Line 65, please insert the phrase -- , and wherein the spray is composed of droplets having a mean diameter of 40-200 microns. -- at end of claim.

Column 31,
Line 29, please insert the phrase -- , and wherein the spray is composed of droplets having a mean diameter of 40-200 microns. -- at end of claim.

Signed and Sealed this

Twenty-ninth Day of June, 2004

JON W. DUDAS
*Acting Director of the United States Patent and Trademark Office*